(12) United States Patent
Echeverry Campos

(10) Patent No.: US 12,180,101 B2
(45) Date of Patent: Dec. 31, 2024

(54) REDUCING COMPOSITIONS AND PROCESSES FOR PRODUCING THE SAME

(71) Applicant: Altered Labs LLC, Miramar, FL (US)

(72) Inventor: Dario Echeverry Campos, Miramar, FL (US)

(73) Assignee: Altered Labs LLC, Miramar, FL (US)

(*) Notice: Subject to any disclaimer, the term of this patent is extended or adjusted under 35 U.S.C. 154(b) by 770 days.

(21) Appl. No.: 15/733,840

(22) PCT Filed: May 31, 2019

(86) PCT No.: PCT/US2019/034925
§ 371 (c)(1),
(2) Date: Nov. 30, 2020

(87) PCT Pub. No.: WO2019/232387
PCT Pub. Date: Dec. 5, 2019

(65) Prior Publication Data
US 2021/0214248 A1    Jul. 15, 2021

Related U.S. Application Data

(60) Provisional application No. 62/679,627, filed on Jun. 1, 2018.

(51) Int. Cl.
| | | |
|---|---|---|
| *C02F 1/70* | (2023.01) | |
| *A01G 25/00* | (2006.01) | |
| *A01K 63/04* | (2006.01) | |
| *A23L 2/02* | (2006.01) | |
| *A23L 2/54* | (2006.01) | |
| *A61K 33/00* | (2006.01) | |
| *A61L 2/18* | (2006.01) | |
| *A61L 101/12* | (2006.01) | |
| *C02F 1/34* | (2023.01) | |
| *C02F 1/44* | (2023.01) | |
| *C02F 101/16* | (2006.01) | |
| *C02F 103/08* | (2006.01) | |
| *C02F 103/20* | (2006.01) | |
| *C02F 103/30* | (2006.01) | |
| *C11D 7/20* | (2006.01) | |
| *C25B 1/04* | (2021.01) | |
| *C25B 1/50* | (2021.01) | |

(52) U.S. Cl.
CPC .................. *C02F 1/70* (2013.01); *A23L 2/02* (2013.01); *A23L 2/54* (2013.01); *A61K 33/00* (2013.01); *A61L 2/18* (2013.01); *C02F 1/34* (2013.01); *C02F 1/441* (2013.01); *C11D 7/20* (2013.01); *C25B 1/04* (2013.01); *C25B 1/50* (2021.01); *A01G 25/00* (2013.01); *A01K 63/042* (2013.01); *A23V 2002/00* (2013.01); *A61L 2101/12* (2020.08); *C02F 2101/163* (2013.01); *C02F 2103/08* (2013.01); *C02F 2103/20* (2013.01); *C02F 2103/30* (2013.01); *C02F 2209/04* (2013.01); *C02F 2209/06* (2013.01); *C11D 2111/12* (2024.01)

(58) Field of Classification Search
CPC .... C02F 1/70; C02F 1/34; C02F 1/441; C02F 2101/163; C02F 2103/08; C02F 2103/20; C02F 2103/30; C02F 2209/04; C02F 2209/06; C25B 1/50; C25B 1/04; A23L 2/02; A23L 2/54; A61K 33/00; A61L 2/18; A61L 2101/12; C11D 7/20; C11D 2111/12; A01G 25/00; A01K 63/042; A23V 2002/00
See application file for complete search history.

(56) References Cited

U.S. PATENT DOCUMENTS

| | | |
|---|---|---|
| 4,235,694 A | 11/1980 | Hall |
| 4,295,865 A | 10/1981 | Su |
| 5,691,293 A | 11/1997 | Kruse et al. |
| 6,290,777 B1 * | 9/2001 | Imaoka ............ H01L 21/02052 257/E21.228 |
| 8,999,173 B2 | 4/2015 | Schwartzel et al. |
| 2001/0029773 A1 | 10/2001 | Helgeson |
| 2004/0118775 A1 | 6/2004 | Murota et al. |
| 2004/0154993 A1 | 8/2004 | Yanagihara et al. |
| 2006/0032754 A1 | 2/2006 | Surikov et al. |
| 2010/0313547 A1 | 12/2010 | Gonze et al. |
| 2011/0059189 A1 | 3/2011 | Cisneros |
| 2012/0115071 A1 | 5/2012 | Fleury et al. |
| 2013/0134046 A1 | 5/2013 | Fanchi |
| 2016/0236158 A1 | 8/2016 | Bauer |
| 2016/0251243 A1 | 9/2016 | Lynn |
| 2018/0134583 A1 | 5/2018 | Bauer |

FOREIGN PATENT DOCUMENTS

| | | |
|---|---|---|
| CN | 1069492 C | 8/2001 |
| EP | 0526099 B1 | 10/1997 |
| EP | 1829826 A1 | 9/2007 |
| JP | 2006-169489 A | 6/2006 |
| JP | 4023970 B1 | 12/2007 |
| WO | WO 96/16555 A1 | 6/1996 |
| WO | 2016168943 A1 | 10/2016 |

OTHER PUBLICATIONS

International Search Report and Written Opinion issued Oct. 31, 2019 in International Application No. PCT/US2019/034925.

(Continued)

*Primary Examiner* — Shirley V Gembeh
(74) *Attorney, Agent, or Firm* — McDermott Will & Emery LLP

(57) ABSTRACT

The present disclosure describes a process for producing a reducing liquid comprising providing a liquid: providing a reducing gas and/or a metasilicate; and infusing the reducing gas and/or the metasilicate to the liquid, for the reducing gas and/or metasilicate to react with the liquid to produce a reducing liquid that has an oxidation reduction potential (ORP) value of about −100 mV or more negative. Further described is the process for preparing a reducing gas, which includes the steps of preparing an activator, introducing the activator into an electrolytic reactor, adding water, and applying a direct current to produce the reducing gas. Also described is a system for producing a reducing liquid.

18 Claims, 10 Drawing Sheets

(56) References Cited

OTHER PUBLICATIONS

Office Action issued in Colombian Patent Application No. NC2020/0016136 dated Dec. 11, 2023, with partial translation.
Examination Report issued in Saudi Arabian Application No. 522441255 dated Dec. 28, 2023, with English translation.
Examination and Search Report issued in United Arab Emirates Application No. P600717/2020 dated Jul. 18, 2024, with English translation.
A.R. Yasmin, S.L. Chia, Q.H. Looi, A.R. Omar, M.M. Noordin, A. Ideris, "Herbal extracts as antiviral agents", Feed additives : aromatic plants and herbs in animal nutrition and health, UK, Elsevier, (Sep. 20, 2019), pp. 115-132.
International Search Report issued in International Application No. PCT/US2023/066656, dated Sep. 19, 2023.
International Search Report issued in International Application No. PCT/US2023/014480, dated Jun. 6, 2023.

\* cited by examiner

Stride Length * = p<0.05; *** = p<0.001; NS = Not statistically significant.

Carpal Flexion * = p<0.05; *** = p<0.001.

Hock flexion. *** = p<0.001.

Forelimb protraction. * = p<0.05; *** = p<0.001.

Hindlimb protraction. *** = p<0.001

REDUCING COMPOSITIONS AND PROCESSES FOR PRODUCING THE SAME

RELATED APPLICATIONS

The present application is a United States National Phase under 35 U.S.C. § 371 of International Application No. PCT/US2019/034925, filed May 31, 2019, which claims the benefit of U.S. Provisional Patent Application No. 62/679,627, filed Jun. 1, 2018, the entire contents of both of which are hereby incorporated by reference for all purposes.

FIELD

The present disclosure relates to the field of chemical processes and compositions. More specifically, the present disclosure describes an electrolytic process for producing a reducing gas and a further process for infusing the reducing gas into a liquid composition with or without a metasilicate. Alternatively the metasilicate may also be infused into a liquid composition without the reducing gas.

BACKGROUND

Oxidation is a chemical reaction that involves the transfer of electrons between reactants. These reactions can produce free radicals, compounds that have unpaired electrons. The production of free radicals can lead to chain reactions that may cause damage to biological and inorganic systems. Prolonged oxidative damage can create serious health problems, decrease the shelf life of commercial products, poison industrial chemical processes, cause structural damage to items of manufacture, and many other problems. To combat oxidative damage, antioxidants or reducing agents are integrated in a wide array of industrial and biological applications. Electrolysis of water has been explored as a potential to produce a reducing gas. Examples of a reducing gas include oxyhydrogen (a.k.a Knellgas), Brown's Gas, Tylar Gas, and HHO Gas (a.k.a. Klein Gas). However, these gases are unstable and reactive, and in some instances have caused serious accidents. For example, after a second accident that hurt two employees, Tylar Gas discontinued production after 2011. In other applications, many industrial reducing agents such as sodium borohydride ($NaBH_4$) are toxic, corrosive to skin, and create environmental hazards. Hence, there is a need to develop a new method that does not have the above drawbacks for producing a reducing gas and an aqueous reducing liquid.

SUMMARY

The present disclosure describes a process for producing a reducing liquid comprising providing a liquid; providing a reducing gas and a metasilicate; and adding the reducing gas and the metasilicate to the liquid, for the reducing gas and metasilicate to react with the liquid, to produce a reducing liquid that has an oxidation reduction potential (ORP) value of about-100 mV or more negative. Each the reducing gas, the metasilicate, and the reducing liquid is non-toxic, non-caustic, and stable.

Also described is an alternative process for producing a reducing liquid comprising providing a liquid; providing either a reducing gas or a metasilicate; and adding the reducing gas or the metasilicate to the liquid, to react with the liquid to produce a reducing liquid that has an oxidation reduction potential (ORP) value of about-100 mV or more negative.

In one aspect, the reducing liquid includes, but is not limited to, organic solvents, nonpolar oils, mineral oils, essential oils, colloidal suspensions, colloidal solutions, leachates from landfills, polychlorinated byphenols (PCBs), and aqueous compositions. The liquid is transformed into the reducing liquid via the electrolytic process described below. Upon completion of the described processes, the reducing liquid gains additional desirable antioxidant physiochemical properties, which can be useful for numerous purposes across all industries. Within the scope of this disclosure are the method and composition, as described above, as applied to a number of specific uses including but not limited to potable water or beverages intended for consumption for all living species; as a cleaner or disinfectant; enhancing laundry processes; and cultivation of aquatic species.

Further within the scope of this disclosure is a system for producing reducing liquid comprising a reaction chamber in fluid communication with a liquid feed stock, a module for producing a reducing gas, optionally, a module containing a metasilicate; wherein the reducing gas and the metasilicate have the capacity to react with the liquid in the reaction chamber to produce a reducing liquid that has an oxidation reduction potential (ORP) value of about-100 mV or more negative.

Still within the scope of this disclosure is a process for preparing a reducing gas. The process comprises (i) providing an activator, wherein the activator comprises water, potassium hydrate, magnesium sulfate, sodium oxidanide, and an alkaline metal silicate; (ii) introducing the activator into a reaction chamber of a reactor, wherein the reactor is configured to produce an electrolytic reaction; (iii) adding water to the reaction chamber to provide a water-activator mixture; and (iv) applying a direct current in the water-activator mixture to produce the reducing gas.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology

BRIEF DESCRIPTION OF THE DRAWINGS

Various features of illustrative embodiments of the disclosure are described below with reference to the drawings. The illustrated embodiments are intended to illustrate, but not to limit, the disclosure. The drawings contain the following figures.

DETAILED DESCRIPTION

Figure 1:
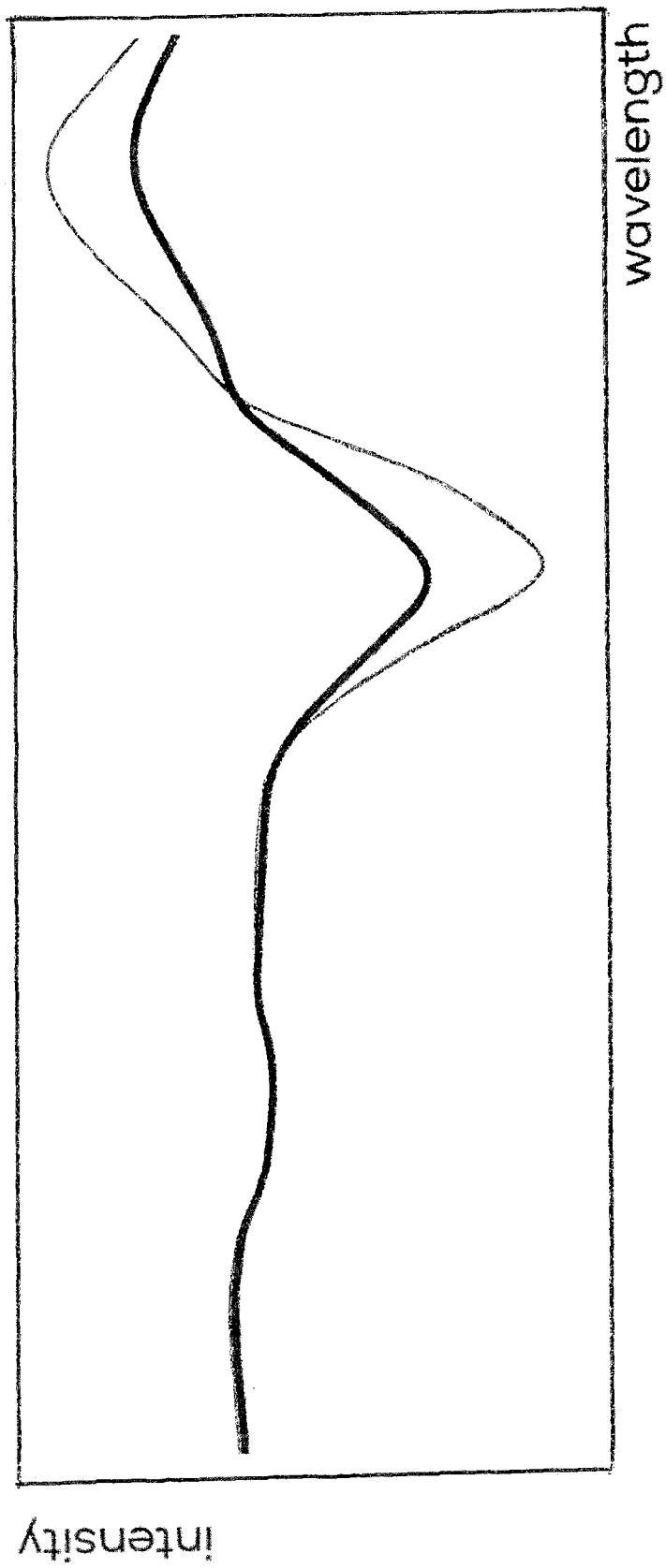
FIG. 1 shows a spectral fingerprint of an infused reducing liquid produced by the process described herein in Example 3. The solid line represents the infused liquid while the dashed line is the fingerprint of reverse osmosis filtered water.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present disclosure. At the very least, and not as an attempt to limit the application of the doctrine of equivalents to the scope of the claim, each numerical parameter should at least be construed in light of the number of reported significant digits and by applying ordinary rounding techniques.

Whenever a numerical range of degree or measurement with a lower limit and an upper limit is disclosed, any number and any range falling within the range is also intended to be specifically disclosed. For example, every range of values (in the form "from a to b," or "from about a to about b," or "from about a to b," "from approximately a to b," and any similar expressions, where "a" and "b" represent numerical values of degree or measurement) is to be understood to set forth every number and range encompassed within the broader range of values.

Processes for producing a non-toxic stable reducing gas and for using the non-toxic stable reducing gas to decrease the amount of undesirable oxidants present in water are needed. This disclosure relates to a process and a system for "restructuring" or transforming a liquid into a reducing liquid. The present disclosure describes a process for producing a reducing liquid comprising providing a liquid; providing a reducing gas and/or a metasilicate; and infusing the reducing gas and/or the metasilicate to the liquid, for the reducing gas and/or metasilicate to react with the liquid to produce a reducing liquid that has an oxidation reduction potential (ORP) value of about-100 mV or more negative. Further described is the process for preparing a reducing gas, which includes the steps of preparing an activator, introducing the activator into an electrolytic reactor, adding water, and applying a direct current to produce the reducing gas. Also described is a system for producing a reducing liquid.

Decreasing the ORP charge to a negative value is desirable because it alleviates the oxidative stress of a system, which is known in the art to be harmful to a particular system. Further, compared to the non-restructured form of the same liquid, the restructured form of the liquid will exhibit additional properties, for example, a pH greater than 7, decreased surface tension, improved hydration, improved bio-assimilation, improved solubility of organic or inorganic compounds with the liquid (such as vitamins, other health supplements, etc), improved detoxification/flush of cells, and improved cellular synthesis. If the reduced composition is intended for human or animal consumption, after restructuring, the liquid still complies with acceptable international standards for ready to drink beverages.

Figure 2:
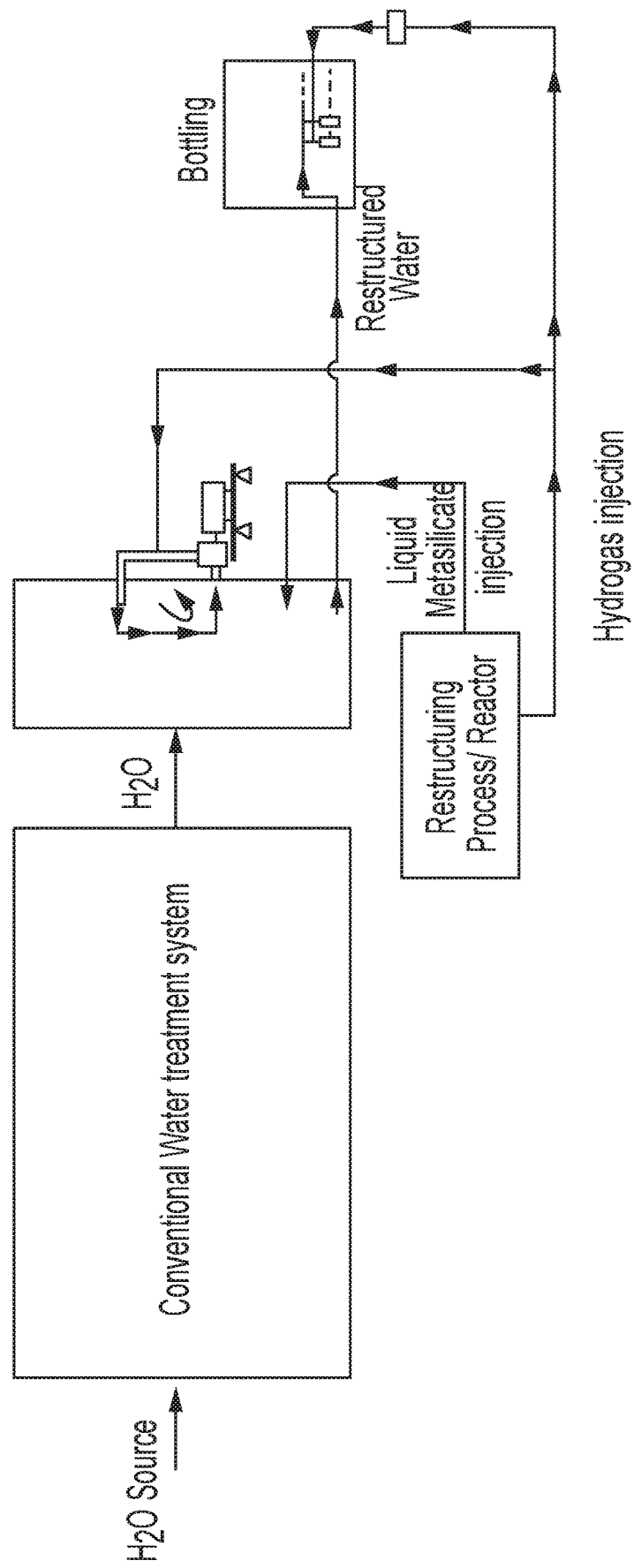
FIG. 2 is a schematic showing of an exemplary system for performing the methods described herein in Example 4. The system is used to perform a process in which a liquid metasilicate is injected into a water tank after it has been treated, and in which a reducing gas is injected into the same water container and also into the bottling process.

FIG. 2 is a schematic showing of an exemplary system for performing the restructuring process. The system is used to perform a process in which a liquid metasilicate is injected into a water tank after it has been treated, and by which a reducing gas is injected into the same water container and also into the bottling process. Reducing gas and/or liquid metasilicate may be added to any conventional water treatment system. The addition can be made at the end of the water treatment process, inside the water treatment tank or reservoir. Both additions are made through conventional infusion systems (membrane dosifying pump for the liquid metasilicate and infusion of the gas at the suction of a conventional recirculating pump in order to create turbulence to improve the efficiency of the mix). The size of the dosifying and recirculating pumps depend on the amount of liquid (typically measured in liters per hour) to be restructured. Additional water gas can be added at the process of packaging. Currently, the infusion of the gas to each bottle is done via conventional nitrogen gas injection system, for example.

Process for Preparing a Reducing Gas

In one aspect, this disclosure relates to a process for preparing an on demand reducing gas. The process comprises the following steps: preparing an activator, wherein the activator comprises water, potassium hydrate, magnesium sulfate, sodium oxidanide, and an alkaline metal silicate; introducing the activator into a reaction chamber of a reactor, wherein the reactor is configured to produce an electrolytic reaction; adding water to the reaction chamber to provide a water-activator mixture; and applying a direct current in the water-activator mixture to produce the reducing gas. It is generally desirable that the pressure in the reaction chamber is reduced to increase the rate of production of the reducing gas. In a preferred embodiment, the reducing pressure in the reaction chamber is maintained at about 0.5 bar. The reactor chamber typically comprises a wet electrolytic cell to propel the electrolytic reduction process as described herein.

Activator Preparation

Activator preparation can be performed using any suitable equipment for conducting chemical reactions involving the activator reagents. Typically, the activator is prepared by combining the activator components in a balanced stoichiometric amounts from the oxidation-reduction equation. In some embodiments, the activator comprises potassium hydrate, magnesium sulfate, sodium oxidanide, and an alkaline metal silicate in a predetermined stoichiometric ratio. The activator can comprise about 40 wt % to about 59 wt % potassium hydrate; about 0.1 wt % to about 5 wt % magnesium sulfate; about 40 wt % to about 59 wt % sodium oxidanide; and about 0.1% to about 5 wt % alkaline metal silicate.

In other embodiments, the activator can comprise about 45 wt % to about 55 wt % potassium hydrate; about 0.2 wt % to about 3 wt % magnesium sulfate; about 45 wt % to about 55 wt % sodium oxidanide; and about 0.2% to about 3 wt % alkaline metal silicate. In other embodiments, the activator can comprise about 47 wt % to about 53 wt % potassium hydrate; about 0.2 wt % to about 1.5 wt % magnesium sulfate; about 47 wt % to about 53 wt % sodium oxidanide; and about 0.2% to about 1.5 wt % alkaline metal silicate. In other embodiments, the activator can comprise about 48 wt % to about 51 wt % potassium hydrate; about 0.3 wt % to about 0.8 wt % magnesium sulfate; about 48 wt % to about 51 wt % sodium oxidanide; and about 0.3% to about 0.8 wt % alkaline metal silicate. Potassium hydrate, magnesium sulfate, and sodium oxidanide are commercially available.

In other embodiments, the activator is a liquid solution comprising potassium hydrate, magnesium sulfate, sodium oxidanide, and an alkaline metal silicate in any of the stoichiometric amounts described herein. The liquid solution can have an activator concentration of about 0.1 to about 20 g/l, about 0.1 to about 15 g/l, about 0.1 to about 10 g/l, about 0.1 to about 5 g/l, about 0.5 to about 4 g/l, about 0.5 to about 3 g/l, about 1 to about 3 g/l, or about 1.5 to about 2.5 g/l.

In other embodiments, the activator comprises alkaline cationic silicate instead of merely an alkaline metal silicate. For example, the alkaline cationic silicate can be selected from the group consisting of an alkaline lithium silicate, an alkaline sodium silicate, an alkaline potassium silicate, an alkaline ammonium silicate, and combinations thereof. The alkaline ammonium silicate can be formed from an ammonium compound having the general formula $NR_4^+$, where R can be selected from the group consisting of hydrogen (H) and a $C_{1-4}$ alkyl group.

The activator can be prepared by any suitable method. For example, the potassium hydrate, sodium oxidanide, alkaline cationic silicate, and magnesium sulfate can be measured out in any of the weight ratios described herein, and subsequently combined to form a single activator mixture. This activator mixture can then be dissolved into water at a predetermined concentration as described hereinabove. Alternatively, a quantity of water can be provided, and the potassium hydrate, sodium oxidanide, alkaline cationic silicate, and magnesium sulfate can be added to the quantity of water in sequence, simultaneously, or combined pairs. In some embodiments, the magnesium sulfate and the alkaline cationic silicate are first mixed into the quantity of water, and the potassium hydrate and sodium oxidanide are subsequently mixed into the quantity of water. Preparation of the activator can be carried out external to a reactor and subsequently added in. Alternatively, the activator can be prepared in a reaction chamber of a reactor.

Preferably, the alkaline cationic silicate is a metasilicate such as an alkaline sodium silicate complex (SSC) or reformed liquid silica (RLS). The metasilicate can be used in the preparation of an activator, and may optionally be added in greater quantities with or without the reducing gas into the source liquid. These complexes are described, for example, in US 20110059189A1, which is incorporated herein by reference. Mass spectroscopic (MS) and nuclear magnetic resonance (NMR) analysis generated a putative empirical formula of the compound or complex to be $Na_{8.2}Si_{4.4}H_{9.7}O_{17.6}$. The formula suggests that alkaline sodium silicate complex (SSC) is not a single compound but a mixture of two different compounds that are in equilibrium with each other. Specifically, the SSC is a mixture of:

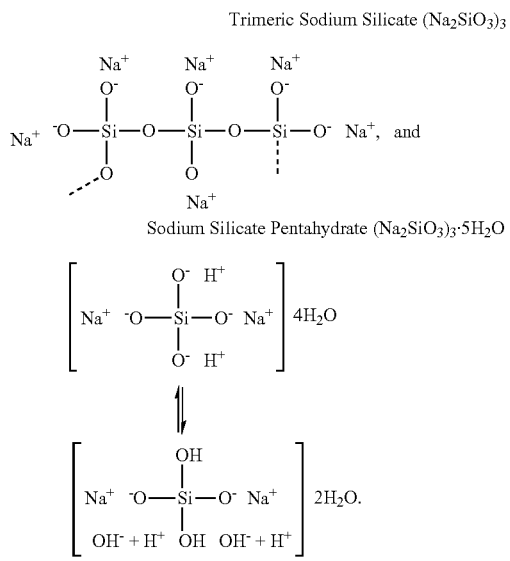

Sodium silicate pentahydrate $(Na_2SiO_3) \cdot 5H_2O$ typically exists in equilibrium as two structural forms, with one form containing one ionized water molecule and the other form containing 3 ionized water molecules. To produce SSC, silicon metal (any grade) is loaded into a reactor. Sodium oxidanide is added along with water. An exothermic reaction occurs. The reaction is allowed to proceed for 4-6 hours, after which the product is collected in a cooling tank. The product is cooled and the obtained liquid product is packaged.

The silicon-based alkaline composition (empirical formula of $Na_{8.2}Si_{4.4}H_{9.7}O_{17.6}$) can have a specific density in the range of 1.24 to 1.26 kg/m³, for example, 1.25±0.1 kg/m³. The composition can also have a pH in the range of 13.8 to 14.0, for example, 13.9±0.1. In some embodiments, the SSC can be dried via any suitable method prior to use in any of the processes described herein. Suitable drying methods include, but are not limited to, mild heating, storage in a desiccator, vacuum drying.

SSC physiochemical properties and potential therapeutic applications have been previously studied. In one study, SSC was found to exhibit antimicrobial properties for gram positive, gram negative, and drug resistant strains as described, for example, in Vatten et al., Res. J. Microbiol. 2012 Mar. 1; 7 (3): 191-8. Sodium silicate is also generally recognized as safe for human consumption by the US FDA pursuant to 21 C.F.R. § 182.90. US 20140087003A1 describes a method using an alkaline sodium silicate composition to inhibit the toxic effects of venom and treat venomous bites and stings. US 20060275505A1 describes a composition for increasing alkalinity in the body containing water, a source of alkalinity; particularly an alkaline silicon solution. US20110059189A1 describes a modified sodium silicate composition, and methods of treating cancer and viral infections utilizing the modified sodium silicate composition ($Na_{8.2}Si_{4.4}H_{9.7}O_{17.6}$), also described in Townsend et al., Int. J. Appl. Res. Nat. Prod. 2010; 3:19-28 (AVAH silicates were also effective in inhibiting several important physiological events important in survival and development of virulence in viral and microbial pathogens). However, the SSC referenced in those publications did not involve a reducing gas, the combination of which is a subject under this description, along with other beneficial uses of this technology.

Reactor and Electrolytic Process

The electrolytic process is generally carried out in a reactor. In an exemplary process, the activator is either prepared within a reaction chamber of the reactor or externally prepared and subsequently added to the reaction chamber. Additional water can be combined with the activator in the reaction chamber in any suitable quantity, including up to the fill capacity of the reaction chamber.

The reactor can be any suitable apparatus for carrying out an electrolytic reaction. In some embodiments, the reactor comprises a wet electrolytic cell. In an electrolytic cell, an electric current is passed from an electronic conductor through a chemical substrate such as an ionic solution contained in one or more cells (i.e., reaction chamber), back into a second electronic conductor. The circuit is closed outside (external circuit) of the cell through various electronic conductors. This typically includes a power supply and a current measuring device. The junctions between the electronic and ionic conductors are called electrodes, namely cathodes and anodes.

In the electrolysis reaction, a direct current is passed through the solution contained in the reaction chamber, producing chemical reactions at the electrodes. In a standard electrolysis of pure water (i.e., without activator present), a reduction half reaction occurs at the cathode in which electrons from the cathode are transferred to hydrogen cations to form $H_2$ gas as illustrated by the chemical equation: $2 H^+(aq) + 2e^- \rightarrow H_2 (g)$. At the anode, an oxidation half-reaction occurs in which electrons are transferred from water molecules to the anode to form $O_2$ gas as illustrated by the chemical equation: $2 H_2O(l) \rightarrow O_2(g) + 4 H^+(aq) + 4e^-$. These half reactions can be balanced with the addition of base.

A direct current (DC) electrical supply is coupled to the reactor and provides the energy necessary to drive the electrolytic process. Electric current is carried by electrons in the external circuit. Electrodes of metal, graphite and semiconductor material are widely used. Choice of suitable electrode depends on chemical reactivity between the electrode and electrolyte and manufacturing cost. A DC electrical power source is connected to two electrodes, or two plates (typically made from some inert metal such as platinum, stainless steel 360 or iridium) which are placed in the water. In some embodiments, the DC delivered to the electrolytic cell is in the range of about 20 V to about 30 V, for example about 24.65 V+0.12 V. The input of electrical current can be further be through a 110 V (60 Hz) or 220 V, 50 Hz or 60 Hz circuit.

The reactor can be configured to perform the electrolytic reaction under reduced pressure or in a vacuum. Vacuum-electrolysis reactors are known in the art and suitable apparatuses will be readily apparent to a person of ordinary skill. The electrolysis reaction can be conducted at standard temperature and pressure (STP). In some embodiments, the reaction is initially conducted at STP, then subsequently, once the production of reducing gas begins inside the reactor chamber, the pressure can be reduced inside the reaction chamber. For example, the reduced pressure can be about 0.3 bar to about 0.9 bar. In some embodiments, the reduced pressure is 0.5±0.05 bar. By performing the reaction under reduced pressure, the rate of production of the reducing gas can be increased by up to 2.2 fold over the reaction performed at standard atmospheric pressure.

Infusion of Reducing Gas into a Liquid

The terms "infuse" or "infusion" or "infusing" or any variation thereof encompasses any other suitable method of mixing reducing gas or silicate with liquid, such as injecting, administering, or applying. In some embodiments, a process is provided for preparing a stable, non-toxic, non-corrosive reducing liquid by infusing a gas produced by the electrolytic process described herein into a "source liquid" to be treated using described processes.

The source liquid can be any suitable liquid that can stably incorporate an infused reducing gas. Examples of suitable source liquids include, but are not limited to, organic solvents, nonpolar oils, mineral oils, essential oils, colloidal suspensions, colloidal solutions, leachates from landfills, polychlorinated byphenols (PCBs), and aqueous compositions. In some embodiments, the source liquid for infusion is water. Sources of water include for example, distilled water, deionized water, tap water, potable water, potable beverages, nonpotable water, agricultural water, irrigation water, salt water, brackish water, fracking waters, water having aqueous heavy metals dissolved therein, industrial water, recycled water, fresh water, water from a natural source, or reverse osmosis water. Potable water is understood to be water safe for human or animal consumption; non-potable water is not safe for human or animal consumption, but can be used in other applications. Fresh water is understood to be water from a natural source that is not salt water. Salt water may be from a natural source such a sea or ocean, it also includes man-made salt water. Industrial water is water that is a used in industrial applications such as manufacturing processes, washing of containers, machines, etc. Industrial water may be tap water, well water, etc that is typically non-potable water. Recycled water is water that is used in a machine, then goes back to a central treatment facility, and then can be returned to the machine, such as a washing machine for laundry. Water used for agricultural purposes includes not only water used for irrigation, but also water that is used for the preservation or disinfection of crops. Water used for the cultivation of aquatic species may include any kind water (including sea water and man-made salt water) necessary for survival of that species encompassing food and other nutrients. For aqueous solutions comprising heavy metals, the heavy metal can be antimony, arsenic, bismuth, cadmium, copper, chromium, iron, mercury, nickel, lead, tin, cobalt, manganese, uranium, or barium.

In some embodiments, the liquid can be an aqueous solution having medium to high biochemical oxygen demand (BOD). BOD is defined as the amount of dissolved oxygen needed by aerobic biological organisms to break down organic material present in a given water sample, most commonly expressed in milligrams of oxygen consumed per liter of sample during 5 days of incubation at 20° C. In some embodiments, the aqueous solution has a 5-day BOD in the range of about 2 mg/L to about 600 mg/L.

Infusion can be conducted by any suitable method. For example, the gas can be infused into the liquid by bubbling the reducing gas into the liquid. The bubbling can be conducted simultaneously with electrolytic production of the reducing gas by coupling the reactor to a container having the liquid therein and flowing the reducing gas into the liquid as it is produced. Alternatively, the infusion can be conducted by bubbling a stored reducing gas, such as in a pressurized gas tank, into a container having the liquid therein.

The infusion process can be augmented by adding the reducing gas to the liquid under turbulent conditions. In fluid dynamics, turbulence or turbulent flow is any pattern of fluid motion characterized by chaotic changes in pressure and flow velocity. Turbulence is caused by excessive kinetic energy in parts of a fluid flow, which overcomes the damping effect of the fluid's viscosity. In general terms, in turbulent flow, unsteady vortices appear of many sizes which interact with each other. Turbulent conditions can be created by a variety of methods that are well-known, which include, but are not limited to, vortexing, shaking, vibrating, mixing, flotation, and cavitation. Turbulence and cavitation improve dissolution rate of the reducing gas into the liquid by up to 100-fold, depending on the application and on the flow capacity of the recirculating pump, typically measured in volume units (e.g. gallons, liters) per minute. In some embodiments, the turbulent conditions are produced by cavitation, wherein the cavitation is conducted using a propeller, impeller, or suitable device. In one example, a recirculating pump is used that contains an impeller, at a rate of up to 3600 revolutions per minute (RPM), preferably 750-900 RPM. Venturi technology is also used when the turbulence is created inside pipes that have a positive flow pressure of liquids.

In producing the stable reducing liquid, the reducing gas is infused into the liquid until a threshold negative ORP is achieved and observed for a sufficient amount of time (stabilization or retention time) to reliably measure the ORP value using a commercially available and calibrated ORP meter with a waterproof electrode, preferably one that can also measure pH. A person of ordinary skill in the art will understand the routine conventions associated with the measurement of reduction potentials, including standard oxidation reduction potentials. This stabilization time will vary depending on the amount of liquid produced per unit of time. In some embodiments, the stabilization time is at least about 2 minutes. In other embodiments, the stabilization time is at least about 10 minutes. More generally, the stabilization time will vary from a few seconds to 28 hours, depending on several factors including the degree of chemical oxygen demand (COD) and the presence or absence of colloidal particulates, oils, solvents and/or others dissolved solutions. Reduced pressure and turbulence will improve the efficiency and thus will reduce the retention time by up to a factor of 100. Appropriate methods for the determination of the appropriate stabilization time for a liquid sample of interest are within the technical knowhow of a person of ordinary skill in the art. The induction of reduced pressure and turbulence will also allow the generation of a "residual effect" in many cases. For example, by applying the correct stabilization time, the infused liquid will maintain a reducing and disinfecting residual effect (i.e. replacing oxidants like chlorine, ozone, UV, $H_2O_2$, etc). In some embodiments, the threshold ORP after stabilization is −150 mV or more negative.

Composite Reducing Liquids

A composite reducing liquid comprising a nontoxic, non-corrosive reducing agent and the infused reducing liquid described herein can also be prepared. The nontoxic, non-corrosive reducing agent can be any compound that is readily miscible with the infused reducing liquid. Suitable reducing agents include, but are not limited to, natural antioxidants for example, ascorbic acid (vitamin c), glutathione, melatonin, and water-soluble tocopherols (vitamin E). In some embodiments, the non-toxic, non-corrosive reducing agent is an alkaline cationic silicate as described herein.

The composite reducing liquid can be produced by any suitable method. In some embodiments, the non-toxic, non-corrosive reducing agent is added in a predetermined quantity to an infused reducing liquid. In other embodiments, the reducing agent and the reducing gas are simultaneously infused into a liquid. This simultaneous infusion can be conducted under turbulent conditions, such as using a recirculating pump at a rate of at least about 800±35 RPM.

The addition can be conducted by quantitative transfer of a single aliquot into the infused reducing liquid. Alternatively, the addition can be conducted by a continuous transfer of the reducing agent from a storage vessel at any desired flow rate over a specific period of time. The flow rate(s) and time will depend on the reducing agent and the desired stoichiometric ratio of reducing agent to infused reducing liquid in the composite reducing liquid. In another embodiment, the reducing agent is added in a punctuated, drop-wise fashion comprising multiple aliquots.

In some embodiments of the process for producing an aqueous reducing liquid, the infusion step of reducing gas, previously described, is performed by infusing 75 to 120 liters per minute of reducing gas per every 60 gallons per minute of the liquid to be restructured, prior to or simultaneously with the alkaline cationic silicate in the range of 0.5 to 12 milligrams per liter. In other embodiments, the quantity of the alkaline cationic silicate required in the process step is in amounts described herein-above, wherein the alkaline cationic silicate comprising of lithium silicate, sodium silicate, potassium silicate, ammonium silicate, or a combination thereof.

In one aspect, the process for preparing a reducing liquid comprising infusing a reducing gas (e.g. a reducing gas produced by an electrolytic process described herein) into a quantity of liquid under turbulent conditions. Inducing turbulence and cavitation in this process increases the efficiency of restructuring the water in the tank up to a thousand fold. It allows for the use of 1 kw of power per every ten thousand (10,000) gallons of water to be restructured per hour. Without the implementation of the cavitation/turbulence system, the rate of dissolution of gas with liquid is inefficient for utility. However, the upper limit for turbulent conditions in this process is less than 3600 RPM because excessive turbulence leads potential cavitation of the impeller of the water pump, which is undesirable for utility.

In some embodiments, the restructuring process comprises the following steps: reducing water gas ("C1") and reducing liquid metasilicate ("C2") are injected immediately before the source liquid enters into any conventional reservoir or container. The source liquid to be treated may go through (i) a closed pressured pipe; or (ii) an open water tank, channel, or open pipe under atmospheric conditions or normal temperature and pressure conditions.

If the source liquid to be treated goes through a closed pressurized pipe, the following steps are further performed: (i) C1 and C2 are injected to the pipe, where C1 is injected via a Venturi apparatus or via another method of creating negative pressure in the pipe; (ii) C2 is proportionally injected via conventional dosing pumps, gravitational dosing methods, or any other method used to dosify liquid chemicals. Negative pressure improves the production of the liquid. Depending on the electrolytic cell, the improvement of gas production can be up to 250%. Different tests conducted show with accuracy that it takes about 9325 liters of C1 gas under NPT conditions to restructure, in about 10 hours, 5000 gallons of water to be treated. This value is equivalent to 932.5 liters of C1 per hour without using enhancing methods of cavitation. The flow of reducing gas (C1) is then measured as flow in liters per hour (FLPH) using a formula that varies depending on the source liquid and other parameters, described further herein for each source liquid and corresponding use. Once the closed pressurized system is stabilized, The ORP value is measured in millivolts (mv). The ORP will vary depending on the composition of the source liquid. The minimum contact time of C1 with the source liquid required inside the pipe is typically between 3 seconds and 30 minutes. The ORP charge is measured after at least 3 seconds of minimum contact time of C1 with the source liquid and should result in a negative value. The formula for calculating FLPH is irrelevant of the liquid pressure inside the pressurized pipe. The volume (milliliters) of liquid metasilicate (C2) required to restructure a source liquid (C2) is determined using a formula described herein-below, which varies based on the composition of the source liquid and its desired use.

If the liquid to be treated goes through atmospheric pressure (open tank, channel or open pipe) or under normal temperature or pressure conditions, then following steps apply for mixing C1 and C2: (i) C1 is mixed with source liquid via under turbulent conditions or via cavitation induced by using flotation modes, recirculating pumps creating vacuum and/or a Venturi apparatus; (ii) C2 is mixed with the source liquid via existing conventional dosing pumps, gravitation dosifiers, or analogous methods apparent to a person with ordinary skill in the art. The FLPH of C1 is in then measured in liters per hour using a formula specific that varies based on the composition of the source liquid and process conditions, described further herein-below which varies based on the composition of the source liquid, process conditions, and the desired use for the source liquid. The volume (milliliters) of liquid metasilicate required to restructure water (C2) is determined using a formula described herein-below, which also varies based on the composition of the source liquid, process conditions, and the desired use for the source liquid. The minimum contact of C2 in the source liquid reservoir or container is typically between 15-30 minutes to achieve a negative ORP. If the residual negative ORP value (mv) is less than-200 mV, then contact time is extended until the ORP is more negative than-200 mV.

Ready to Drink Reduced Water and Beverages for Consumption

One aspect and specific application of the restructuring process is to prepare potable or "ready to drink" (RTD) water or other beverages for human and nonhuman (animals) consumption. The restructuring process described herein-above can be applied to any water based product suitable for human and nonhuman consumption including but not limited to drinking water, carbonated beverages, juices, colored beverages, organic beverages, teas, coffees, energy drinks, CBD beverages containing cannabinoid oil, and any other beverage with added organic and/or inorganic chemical components. Wherein, the reduced drinking water is (1) substantially free of alkaline chemicals, such as but not limited to, sodium or potassium hydroxide or sodium bicarbonate; and (2) substantially free of oxidants, such as but not limited to, calcium hypochlorite, sodium hypochlorite, gaseous chlorine, bromine, iodine, ozone, or ultra violet light. An additional benefit of the reducing or restructuring process is that the original color, taste, and odor of the reducing drinking water is preserved. Substantially free refers to oxidant quantities less than about 1%, preferably less than about 0.1% for the indicated matter.

Further, after undergoing the restructuring process, despite an alkaline pH of over 9.5, the reduced water remains non-caustic, and nontoxic to humans and animals upon consumption, including even highly alkaline pH of over 13.0. The addition/infusion of the liquid metasilicate is not chemically induced, nor produced by alkaline chemicals (such as sodium hydroxide, sodium bicarbonate, etc).

Under normal conditions of preservation and handling, the hydration (surface tension) and alkalinity (pH) stay stable for at least 12 months after the restructuring process. Stability studies were conducted adding 1.0 mg/liter of SSC to (i) a 55 gallon drum made of BPA plastic human grade (with zero UV penetration); (ii) IL metallic bottles; (iii) IL glass bottles; (iv) IL plastic bottles. The reducing gas was infused into each container with a contact time of 30 minutes. Post stabilization, the pH was measured to be around 10. The drum and bottles were sealed was then kept outside under atmospheric conditions for two years in Florida, USA. After two years, the pH of the water bottle was still around 10, without any microbial growth.

The stability of the liquid water is increased because the reducing drinking water is substantially free of oxidants because they are effectively neutralized via the reduction process, particularly oxidants such as of calcium hypochlorite, sodium hypochlorite, gaseous chlorine, bromine, iodine, ozone, or ultra violet light.

The processes described herein can be used to restructure RTD beverages with additional physical, chemical, organoleptic, and bacteriological properties via the use of a reducing water-based gas and a stable reducing liquid metasilicate, which is alkaline, non-caustic, and nontoxic to humans and animals upon consumption. Such restructuring converts the ORP from a positive to negative value. In some embodiments, the reducing drinking water has an ORP value of about −300 mV, ranging from −200 mV to −400 mV. The electrolytic process releases free electrical charge via the water based reducing gas and the liquid metasilicate and its reducing, high alkaline, non-caustic, and nontoxic properties. For RTDs with high levels of ready to be oxidized organic matter (juices, teas, etc), the process of pasteurization can be replaced in part or in full by the process of this disclosure, the need for refrigeration can also be replaced in part or in full. The process can be calculated to then reduce in full or in part the oxidation processes inside any RTD beverage.

In some embodiments, the process to produce the reduced RTD water or beverage comprises of the following modified steps to the restructuring process: First, the reducing water gas and reducing liquid metasilicate are added to the tank that contains the RTD beverage immediately before the bottling process. To comply with the standards for a specific country/region/city where the RTD is going to be purchased or sold, the ORP value of the RTD liquid in the tank is lowered to minimum-300 mV or more negative. In order to obtain an ORP value of −300 mV, it requires between 25 to 35 minutes of initial contact time. Then, a minimum retention time of 30 minutes at −300 mv of ORP is required. Packaging or bottling as used herein includes any suitable process for placing reducing liquid into suitable portable containers such as bottles, barrels, cartons, cans, ampules or another functionally equivalent device of any size or material.

The properties of restructured water are secured before the bottling process. For example, once retention time of 30 minutes is reached with a minimum of −300 mV and the desired pH value of 13.0, the restructured water is maintained out of the reach of solar rays, potential air contamination, or other forms of undesirable contamination. One way this is achieved is by keeping the restructured water in the water tank perfectly sealed. It is preferable to bottle the restructured water within the next 4 hours after the restructuring process and retention time are completed.

Optionally, water gas is infused (e.g., at a flow rate of 100 to 145 liters per hour) immediately before sealing the cap of each bottle. The pressure of infusion of the gas is typically between 3.5 and 4.0 PSI at normal temperature and atmospheric pressure. An increase of pressure can be considered by adding 0.20 PSI per every 3,000 (three thousand) feet increase in altitude. No corrections are needed for variations in temperature and humidity, as long as the freezing point is not reached.

Potabilization & Pretreating Industrial Water for Washing, Disinfectant and Cleaning Purposes Another aspect of the disclosure is to restructure industrial water as a pretreatment method for washing, disinfectant, and cleaning purposes, for example prior to the production of RTD bottled beverages. Currently, water treatment plants typically use prefiltration, ultrafiltration, and reverse osmosis to purify and disinfect water. Transforming the ORP of water from positive to negative by the addition of the electrical charge through the reducing gas has the additional properties of (1) replacing and/or enhancing surfactant(s) and (2) serving as a disinfectant that kills 99.9% of bacteria and fungi, see for example, Vatten et al., Res. J. Microbiol. 2012 Mar. 1; 7 (3): 191-8. In another study, an alka-hydroxy product (Mastisil®), consisting of SSC diluted 2.0% in tap water demonstrated complete inhibition of growth of three gram-negative bacteria (*E. coli* K-12, *E. coli* O157: H7, and *S. enterica*). However, the three Gram-positive bacteria (*E. faecalis, S. aureus*, and *S. pyogenes*) tested showed greater resistance. The Minimum Inhibitory Concentration (MIC) of the product was the 2.0% for *S. aureus* and 3.0% for *E. faecalis* and *S. pyogenes*, although partial inhibition was seen at lower concentrations for all three of these organisms. Mastisil for the Dairy Cow Industry, Cisne Enterprises (Odessa, Texas).

In one aspect, the reducing water gas and reducing liquid metasilicate are used as a catalyst to enhance most if not all of the existing conventional potabilisation methods and processes that are certified worldwide. This application allows for a substantial reduction of conventional chemicals used in the potabilisation methods. It also establishes new parameters for the control and prevention of biofilms inside pipes, liquid tanks or containers, and closed loops. The reduction process is expected to decrease up to 90% human consumption of any type of oxidants such as calcium hypochlorite, sodium hypochlorite, gaseous chlorine, bromine, iodine, ozone, and ultra violet light. Further, this method reduces the internal oxidation of metal pipes up to 90% by keeping the water restructured at all times. In another aspect, the reducing liquid after undergoing the restructuring process can be used for washing and disinfecting purposes during the bottling step of the drinking water or another source liquid without the use of caustic chemicals or harmful alkalizers.

In one embodiment of the enhanced potabilisation or disinfection process, reducing water gas and reducing liquid metasilicate are first injected (regardless of the potabilisation system used) prior to the commencement of the water treatment method. Water to be treated goes through a closed pressurized pipe or through an open tank, container, channel or pipe under atmospheric conditions. If the water to be treated goes through a closed pressurized pipe, pursuant to the steps of the restructuring process described hereinabove, the FLPH required to restructure 5000 gallons of water in about 10 hours, is determined using the formula FLPH=Y×111.9×FGPM, where Y=1+ (IORP/470). FGPM represents the flow of water measured in gallons per minute. IORP represents the initial ORP value in mV. Y is an ORP coefficient correlating the IORP of a liquid to be restructured and the additional flow of gas needed to obtain similar final results. The IORP value for the different formulas also depends on the specific application. The constant values also fluctuates from 22.38 to 223.8 depending on the source of the liquid and its desired use. In this particular formula, 470 represents the average positive ORP of the source liquid, which will vary with each sample. The minimum contact time of reducing water gas inside the pipe is 3 seconds and the minimum ORP obtained after 3 seconds is −90 mV. Volume of the reducing liquid metasilicate in milliliters (C2) is equal to 0.2×Y×volume of water (VW) to be treated in liters, also expressed as the formula C2=0.2×Y×VW. Different tests conducted show with accuracy that it takes about 9325 liters of reducing water gas under normal temperature and pressure conditions to restructure in about 10 hours 5000 gallons of water to be treated. Alternatively, if the water to be treated goes through an open pipe or container under atmospheric conditions, pursuant to the steps of the restructuring process described hereinabove, the FLPH is determined using the formula FLPH=Y×22.38×FGPM, where Y=1+ (IORP/470). Minimum contact time of C1 in the tank is 30 minutes. Minimum ORP obtained after 15 minutes is −200 mV. The volume of the reducing water gas in milliliters (C1) is calculated using the formula C1=0.2×Y×VW, where VW is the volume of source liquid in liters.

In another embodiment, the restructuring process can be used to enhance prewash and wash cycles achieving additional disinfectant benefits. The volume of water used is in the restructuring process is equal to conventional volumes typically used. There are two different possibilities to produce the restructured washing water: (i) via a separate water tank or (ii) via restructuring the disinfectant water directly through the water pressurized line. If the water to be treated goes the through a closed pressurized pipe, pursuant to the steps of the restructuring process described herein-above, the FLPH is determined using the formula FLPH=Y×223.8×FGPM, where Y=1+ (IORP/470). Minimum contact time of C1 inside the pipe is 3 seconds. Minimum ORP obtained after 3 seconds is −90 mV. The formula is irrelevant of the water pressure inside the pressurized pipe. The volume (mL) of the reducing liquid metasilicate (C2) is calculated using the formula: C2=1.6×Y×VW. The different tests conducted show with accuracy that it takes about 18,650 liters of C1 gas under normal pressure and temperature conditions to restructure in about 10 hours 5000 gallons of water to be converted in disinfectant restructured water. Alternatively, if the water to be treated goes through an open pipe or container under atmospheric conditions, pursuant to the steps of the restructuring process described herein above, the FLPH is determined using the formula FLPH=Y×22.38×FGPM, where Y=1+ (IORP/470). Minimum contact time of C1 is 30 minutes. Minimum ORP obtained after 15 minutes is −290 mV. The volume (mL) of reducing liquid metasilicate (C2) is calculated using the formula: C1=1.6×Y×VW, where VW is the volume of source liquid in liters. The different tests conducted show with accuracy that it takes 1865 (one thousand eight hundred and sixty five) liters of C1 under NPT conditions to restructure in about 10 hours 5000 gallons of water to be treated.

Enhancement of the Pasteurization Process

Since Mr. Louis Pasteur invented the pasteurization in the mid-1880s, no additional equivalent methods have been launched. Pasteurization neutralizes enzymes and bacteria by heating the liquid to a specific temperature for a specified period of time. Pasteurization also destroys or decomposes in whole or in part organic matter (nutrients), and the nutritional value of foods is diminished. Heating is an oxidative process commonly used in pasteurization. Here, the restructuring process can also be used to enhance pasteurization or replace it entirely without adding any heat. The final result of this restructuring process is to complement and/or replace pasteurization by neutralization of any oxidation process in the liquid/beverage, before, during, or after the pasteurization process. In some aspects, the reducing gas and the reducing metasilicate may be added into the liquid (e.g. juice, milk) to be pasteurized either during the conventional pasteurization process or as the last step immediately before bottling. This process does not change if the critical acidity of the beverage (e.g. juice, cider, tea) is above or below the reference pH of 4.6. Additionally, this restructuring process achieves results that are comparable to or better than conventional methodologies used in the market for pasteurization (tunnel, microwave, heat exchanger, death ray bath, STHT, etc).

In this application of the methods described herein, the restructuring process may be applied (i) immediately before the conventional pasteurization or disinfection process (if process occurs before bottling); or (ii) at the end of the pasteurization process as the last step before bottling. In both cases, the following formulas apply, regardless if the pasteurization or disinfection occurs in an open atmospheric tank or in a pressurized pipe. FLPH=Y×223.8×FGPM, where Y=1+ (IORP/150). Minimum ORP is (−) 90 mV. The formula is irrelevant of the water pressure inside the pressurized pipe. The formula for the application of the reducing liquid metasilicate is C2=1.6×Y×VW. Further, the addition of the reducing metasilicate depends on the following factors and suppositions: (1) the pasteurization enhancement can be accomplished just with the addition of the reducing gas following the formula above; (2) additional reducing/antioxidant/alkaline properties can be added to the pasteurized liquid by adding the reducing metasilicate; (3) the final value of the pH of the liquid can be restructured to be slightly acidic up to highly alkaline; and (4) no significant changes in taste or odor have been detected. Ultimately, the final product design of the liquid RTD depends on the desired result.

Enhancement of Wet Laundry Processes

The laundry processes described in this disclosure are related to the processes comprising water as the primary solvent, humidifier, and mode of mixing chemicals, collectively referred to as the wet laundry process (WLP). After the restructuring process, it is important that different types of waters described herein above stay as acceptable washing water under international standards. If water recycling methods are used, the recycled water will also be restructured. This is not a water purification/potabilisation system by itself. The WLP introduces not only a negative charge, but also surfactant and disinfectant properties that transform any washing water into a complementary or alternative detergent for this specific purpose. Further, the obtained restructured water used for washing can additionally have its pH value elevated up to values above 13.0 without being caustic or toxic to the linen or the environment. An important feature of the WLP is the use of reducing water gas and reducing liquid metasilicate as a catalyst under specific mixes and compositions, to enhance conventional washing methods.

Additional properties given to the source washing water in the WLP, for example, includes: reduction of the surface tension of the water due to negative charge; non-caustic increase of the pH value of either recycled water or non-recycled water; change of the ORP charge of the recycled or non-recycled water from positive to negative; improved reaction with surfactants (such as detergents or cleaners) and disinfectants; improved solubility of organic and inorganic materials present in the laundry (e.g., linen); less laundry (e.g., linen) weight loss; reduction in allergic skin reactions compared to conventional cleaning agents in wet laundry; reduction in energy consumption due to the decrease in temperature needs and mechanical cycles; and substantial reduction of effluents, pollution and hazardous chemicals. It also establishes new parameters for the control and prevention of hazardous biofilms inside pipes, tanks and closed loops. It reduces up to 90% the consumption of any type of oxidants (disinfectants) like calcium hypochlorite, sodium hypochlorite, gaseous chlorine, bromine, iodine, ozone, Ultra violet light, hydrogen peroxide, etc.

Further the described WLP process reduces the internal oxidation of metal pipes up to 90% by keeping the restructured water with reducing properties at all times. In one study, two glass containers each with 500 ml of city water with 7 iron nails were prepared. One container was treated with the restructuring process with 1.0 mg/liter of SSC and by infusing the reducing gas at a rate of 75 liter per hour for 10 minutes. After 8 hours, the restructured beaker did not show any signs of oxidation (rust) on the iron nails, while the iron nails in the untreated breaker showed clear signs of rust formation resulting from oxidation of iron.

This application does not require change, nor modify any of the machines and equipment used in the conventional washing systems. This application only uses reducing water gas and reducing liquid metasilicate as additives or catalysts to be injected during the different steps of the washing processes. This application is an enhancement, a complement and a synergy to the existing systems and machines. In some specific cases (mostly hospitality laundry), the synergy and the enhancement become so efficient that it is possible to reduce up to 100% the use of all chemicals and to replace them in full with the use of reducing water gas and reducing liquid metasilicate.

The application of the restructuring process can improve, enhance or replace the "four pillars" of laundry and sanitation processes. The four pillars or key variables of laundry consist of temperature, time, use of certain chemicals, and mechanical processes for cleaning garments. In some aspects, additional chemicals such as organic liquid or solid certified components may be added in order to enhance surfactants and disinfection (i.e. plant esters, organic acids, etc.) and reduce the overall time for the WLP. Using the restructuring process of this disclosure allows, temperature to be lowered up to ambient water temperature (as long as ambient water temperature is not lower than 70 degrees Fahrenheit). Further, duration (and number of cycles) for WLP, mechanical cycles, and quantity of chemicals can be substantially decreased. In some instances, use of undesirable conventional chemicals can substantially be eliminated, i.e., they are replaced with the reducing gas and the liquid metasilicate. Importantly, the process introduces a negative ORP charge (around-300 mV) as a new parameter that was not previously considered in the context of WLP.

In this application of the method, the WLP comprises essentially the same restructuring process as described herein-above, wherein reducing water gas (C1) and reducing liquid metasilicate (C2) are injected right before industrial source water enters into any conventional washing machine or system. If the water to be treated goes through a closed pressurized pipe, pursuant to the steps of the restructuring process described hereinabove, the FLPH is determined using the formula $FLPH=Y \times 111.9 \times FIGPM$, where $Y=1+ (IORPI/50)$. FIGPM represents the flow of industrial water measured in gallons per minute. IORPI represents the initial ORP value of industrial water in mV. The minimum contact time of C1 required inside the pipe is 3 seconds. Minimum ORP required after 3 seconds is −90 mV. Different tests conducted show with accuracy that it takes about 9325 liters of C1 gas under normal pressure and temperature conditions to restructure in about 10 hours 5000 gallons of water to be treated. The formula is irrelevant of the water pressure inside the pressurized pipe. The volume (mL) of liquid metasilicate required to restructure the volume of industrial water (VWI) is determined using the formula $C2=0.35 \times Y \times VWI$, where VWI is measured in liters and C2 is in milliliters.

When the water to be treated goes through an open pipe or container under atmospheric conditions, pursuant to the steps of the restructuring process described herein-above, the FLPH is determined using the formula $FLPH=Y \times 22.38 \times FGPM$, where $Y=1+ (IORP/50)$. The minimum retention time of industrial water (mRTI) with C1 and C2 is greater than or equal to 15 minutes. If after mRTI the residual negative ORP value (mv) is less than-200 mV, then $FLPH=S \times Y \times 22.38 \times FGPM$ where $S=1, 2, 3, 4 \ldots$ until the residual negative ORP value is more negative than-200 mV. S is a coefficient that represents the actual resistance of the source liquid to achieve negative ORP; S is always a positive value. The different tests conducted show with accuracy that it takes about 1865 liters of C1 under NPT conditions to restructure 5000 gallons of water to be treated. The volume (mL) of liquid metasilicate required to restructure the volume of industrial water (VWI) is determined using the formula $C2=0.2 \times Y \times VWI$, where VWI is measured in liters. C2 is then here the amount in milliliters of liquid metasilicate required to restructure the volume of industrial water (VWI) as determined using the formula $C2=0.2 \times Y \times VWI$, where C2 value is obtained in milliliters and VWI value is in liters.

In another application, the process is used for the enhancement of the disinfection and washing of the industrial areas where only fresh water quality or better must be used for this application. After undergoing the restructuring process described herein, the restructured water may be used to spray a mist to prevent and control air bacterial and fungi contamination. The restructured water mist can be sprayed at the beginning of the ironing process in to all the surface of the different types of garments or linens (e.g., blankets, pillows, etc) to prevent static formation in the ironing machines. The volumes of water produced are kept equal to the ones conventionally used.

This combination of reducing water gas (C1) and reducing liquid metasilicate (C2) produces a package of reducing compositions and processes for the specific niches in the laundry industry described here. The added properties of the restructured water create a new set of compositions, methods and processes for the conventional laundry industry that are much more favorable to the final quality of the linen, the environment and to decrease energy consumption.

There are two different possibilities to produce the restructured washing water: Either (1) via a separate water tanks; or (2) via restructuring the disinfectant water directly through the pressurized water. If water to be treated goes through a closed pressurized pipe, the wash step in the enhanced laundry process is performed according to the formula $FLPH=Y \times 223.8 \times FGPM$, where $Y=1+ (IORP/470)$. The minimum contact time of C1 inside the pipe is 3 seconds and minimum ORP obtained after 3 seconds is −90 mV. The formula is irrelevant of the water pressure inside the pressurized pipe. Only fresh water quality or cleaner must be used for this application. The volume of C2 (milliliters) is calculated using the formula: $C2=1.6 \times Y \times VW$. The different tests conducted show with accuracy that it takes about 18,650 liters of C1 gas under normal pressure and temperature conditions to restructure in about 10 hours 5000 gallons of water to be converted in disinfectant restructured water.

If the water to be treated goes through atmospheric pressure (open tank, channel or pipe), then the FLPH is determined using the formula $FLPH=Y \times 22.38 \times FGPM$, where $Y=1+ (IORP/470)$. Where the with minimum retention time of industrial water (mRTI) with C1 and C2 is greater than or equal to 15 minutes and minimum ORP value (mv) is −290 mV. No variations of this formula are needed, because fresh water or cleaner is used. The volume (milliliters) of liquid metasilicate (C2) required to restructure the volume of water (VW) is determined using the formula $C2=0.2 \times Y \times VWI$, where C2 value is obtained in milliliters and VW value is in liters. Different tests conducted show with accuracy that it takes about 1865 liters of C1 to restructure in about 10 hours 5000 gallons of water under normal pressure and temperature conditions.

Aquatic Species

There is increasing demand in the fishing industry to harvest aquatic species more efficiently. Problems related to increased density, mortality, infections, handling, etc. have led to inefficiencies in being able to grow and sell fish. Fish tanks accumulate organic waste, ammonia, oxidative species, and have decreased levels of oxygen that are lethal to fish if left unfiltered. In this application, restructuring aquatic farming water stops and neutralizes the different oxidation and nitrification processes due to the high reducing properties of the restructured water. Adding air or dissolved oxygen to the process improves the final efficiency of the system. Further, the restructuring process can be used as an emergency system when oxygen levels in the fish tank are critically low, perhaps due to a damaged or insufficient oxygen supply. This emergency application allows some aquatic species to survive even days, instead of hours, while the system is brought back to its ideal state. However, the restructuring process does not replace aeration or pure oxygen infusion in the daily operation of a fresh water species location.

The process is applicable for closed volumes of water (tanks, pools, lakes preferably not bigger than one million gallons, etc). The described restructuring process is applicable in an variety of source water including, but not limited to, sea water, artificial sea water, fresh water, brackish water, dechlorinated city water, reverse osmosis water, etc. All the types of water mentioned above have a positive ORP (typically between +50 mv to +750 mv). After undergoing the restructuring process, water ORP value becomes negatively charged, typically between −100 mV and −900 mV.

The restructuring process can also serve as a hydration process under specific conditions for fresh water species. In one example, increased hydration of the aquatic species leads to weight gain, which ultimately increases its price. In another example, the restructuring process serves has a preservative preventing further oxidation of a dead fish without chemicals such as chlorine, bicarbonates, or anhydrous tripolyphosphate. Further, given the reducing properties of the restructuring process and the resulting water, consumption of oxidants is decreased by up to 90%; example of such oxidants include calcium hypochlorite, sodium hypochlorite, gaseous chlorine, bromine, iodine, ozone, ultra violet light, hydrogen peroxide, etc. Further, the restructuring process also reduces the internal oxidation of metal pipes up to 90% by keeping the restructured water in a reduced state.

In this application, reducing gas and liquid metasilicate are typically injected right before fresh water or recycled water enter into any conventional reservoir where the fresh water species are held. The source water may go through (i) a closed pressured pipe; or (ii) an open water tank, channel, or open pipe subject to atmospheric pressure. If the source water goes through a closed pressurized pipe, the flow of reducing gas (measured in liters per hour) is determined using the formula $FLPH=Y\times111.9\times FIGPM$, where $Y=1+(IORPI/50)$. FIGPM is the flow of industrial water measured in gallons per minute. IORPR is the initial ORP of recycled water. Once the system is stabilized, the ORP value is typically between +100 mV and −150 mV, but may vary based on the percentage of fresh water mixed with used water. The minimum contact time of C1 required inside the pipe is 3 seconds. Minimum ORP required after 3 seconds is −90 mV. The formula is irrelevant of the water pressure inside the pressurized pipe. The volume (milliliters) of liquid metasilicate required to restructure water (C2) is determined using the formula $C2=0.35\times Y\times VW$, where the water may be fresh water or recycled water. Different tests conducted show with accuracy that it takes about 9325 liters of C1 gas under normal temperature and pressure conditions to restructure in about 10 hours 5000 gallons of water to be treated.

If the water to be treated goes through atmospheric pressure (open tank, channel or open pipe), FLPH is calculated using the formula: $FLPH=Y\times223.8\times FGPM$, where, $Y=1+(IORP/470)$. The volume (milliliters) of liquid metasilicate required to restructure water (C2) is determined using the formula $C2=0.2\times Y\times VW$. Minimum contact time of C2 in the tank is 30 minutes and the minimum ORP obtained after 15 minutes is −200 mV. If the residual negative ORP value (mv) is less than-200 mV, then $FLPH=S\times Y\times22.38\times FGPM$ where $S=1, 2, 3, 4 \ldots$ until residual negative ORP value (mv) is more negative than-200 mV. The volume (milliliters) of liquid metasilicate required to restructure water (C2) is determined using the formula $C2=0.2\times Y\times VW$, where the water may be fresh water or recycled water. The different tests conducted show with accuracy that it takes about 1865 liters of C1 under normal temperature and pressure conditions to restructure in about 10 hours 5000 gallons of water to be treated.

In a particular application, the restructuring process steps are used at a fresh water species production facility. Here, the same steps mentioned herein-above apply for either when (i) the water to be treated goes through a closed pressurized pipe; or (ii) water to be treated goes through atmospheric pressure (open tank, channel or pipe). If the water to be treated goes through a closed pressurized pipe, FLPH is calculated using the formula: $FLPH=Y\times223.8\times FGPM$, where, $Y=1+(IORP/470)$, only fresh water quality or better must be used for this application. Minimum contact time of C1 inside the pipe is 3 seconds and the minimum ORP obtained after 3 seconds is −90 mV. The volume (milliliters) of liquid metasilicate required to restructure water (C2) is determined using the formula $C2=1.6\times Y\times VW$, where the water is also fresh water quality or better.

If the water to be treated goes through atmospheric pressure (open tank, channel or open pipe), FLPH is calculated using the formula: $FLPH=Y\times22.38\times FGPM$, where, $Y=1+(IORP/470)$. In this embodiment, minimum retention time of C1 in the tank is greater than or equal to 15 minutes and the minimum ORP obtained after 15 minutes is −290 mV. The volume (milliliters) of liquid metasilicate required to restructure water (C2) is determined using the formula $C2=1.6\times Y\times VW$. The different tests conducted show with accuracy that it takes about 1865 liters of C1 under normal temperature and pressure conditions to restructure in about 10 hours 5000 gallons of water to be treated.

The restructuring process is also applicable to different types of salt water. The reducing gas and liquid metasilicate are used as a catalyst under specific mixes and compositions, to enhance existing conventional methods and processes that are certified worldwide to keep the salt water species alive, healthy, reproducing efficiently, and growing with acceptably low mortality and good conversion rates. The application of reducing liquid metasilicate is not as necessary as in the fresh water applications because salt water species do not require much metasilicate; typically the metasilicate is used in parts per billion instead of parts per million. The liquid metasilicate amount to be injected is specific to each salt water species. In some embodiments a liquid metasilicate is not needed.

The steps in the process for restructuring of salt water is substantially the same as described hereinabove, wherein C1 and C2 are injected right before fresh ocean or man-made salted water (that has not been mixed with used and contaminated waters) or recycled salt water enter into any conventional reservoir where the salt water species are held. Next, the water to be treated may go through a closed pressured pipe or open tank, channel, or open pipe under normal atmospheric conditions. For closed pressurized pipe, flow of reducing gas (C1), measured in liters per hour is calculated using the formula $FLPH=Y\times111.9\times FIGPM$, where $Y=1+(IORPIS/50)$. FIGPM is the flow of industrial water measured in gallons per minute. IORPS is the initial ORP of fresh salt water, this value is always positive. Most of the salt waters to be treated around the world have an IORP between +550 mV and +150 mV. The minimum contact time of C1 required inside the pipe is 3 seconds. Minimum ORP required after 3 seconds is −90 mV. The formula is irrelevant of the water pressure inside the pressurized pipe. The volume (milliliters) of liquid metasilicate required to restructure the volume of salt water (C2), is determined using the formula C2=0.35×Y×VW. The water (VW) can be either fresh or recycled salt water. Different tests conducted show with accuracy that it takes about 9325 liters of C1 gas under normal temperature and pressure conditions to restructure in about hours 5000 gallons of water to be treated.

For open tank, channel or open pipe subject to atmospheric conditions, flow of reducing gas (C1), measured in liters per hour is calculated using the formula FLPH=Y× 22.38×FGPM, where Y=1+ (IORPS/50), also where minimum retention time is greater than or equal to 15 minutes. If after minimum retention time is accomplished, the residual negative ORP value (mv) is less than (−200 mv), then FLPH=S×Y×22.38×FGPM where S=1, 2, 3, 4 . . . until residual negative ORP value (mv) is −200 mV or more negative. The volume (milliliters) of liquid metasilicate required to restructure the volume of salt water (C2), is determined using the formula C2=0.2×Y×VW, where VW is the volume of salt water in liters. The different tests conducted show with accuracy that it takes about 1865 liters of C1 under normal temperature and pressure conditions to restructure in about 10 hours 5000 gallons of water to be treated.

The restructuring process can be used in food pellets for aquatic species to serve as a preservative to extend shelf life and inhibit growth of bacteria and fungi over an extended period of time compared to conventional methods without the use antibiotics or antifungal agents. This application introduces several additional processes during the production of the pellets, during the hydration of the pellets and during the storage of the pellets. Most pelleted foods get exposed to humidity, as well as growing fungi and bacteria. Additionally, if during the process of forming and mixing the components of the pellets a correct enhancer is added, the end product will be improved in terms of assimilation, conversion, nutrition.

The addition of the reducing liquid metasilicate and the use of the reducing water during the different stages of production of the pelleted food leads to several benefits. For example, first, increase in moisture migration within pellets by reducing hydrogen bonding between water molecules. Second, increase in moisture absorption by the starch/protein matrix. Third, promotion of the process of water hydration onto starch which results in the starch becoming gelatinized. Fourth, improvement of dry matter digestibility, protein digestibility. Fifth, stabilization of pH to high alkaline levels with presence of antioxidants.

The method for production of the restructured pelleted food is specific for each species and for the age of each species. By regularly spraying restructured water in storage areas and immediately prior to packaging, there the rate growth of mold and bacteria is reduced.

Restructured Ice

The process described hereinabove may be used to generate restructured ice as a preservation method for increased shelf life for foods referred to as "Restructured & Energized Ice" or "REICE." The reducing gas and liquid metasilicate are used as an additive/catalyst in a more concentrated formula under specific mixes and compositions. Keeping food close to the freezing point stops or prevents further oxidation. REICE is made by adding one more step at the end of the production of the water—the phase change of water from liquid to ice upon lowering temperature. Ice is the most common preservative for food around the world. Bacteria stays latent and dormant in regular ice, increasing the risk of bacterial contamination. High doses of disinfectant chemicals cannot be used with ice because it will change the texture, flavor, smell and/or color of the aquatic species or other food exposed to such ice, making it undesirable for sale and consumption.

It is expected that REICE will prevent bacterial contamination better than regular ice based on chemistry and biology principles apparent to one skilled in the art. REICE is a reducing disinfectant, bactericide, and fungicide attributable to a reduced oxidative state further enhanced by the antimicrobial properties of SSC as previously described. Even after melting completely, REICE maintains these reducing properties. If melted in fresh or salt water, REICE proportionally restructures the water-REICE mixture.

In one aspect, REICE can be used to prevent bacterial and fungal contamination in the fresh or salt water species industries. Once correctly restructured, so long as it stays mostly frozen, REICE maintains the same properties as restructured water. REICE is designed to have a negative ORP value (millivolts) and a highly alkaline pH (ranging from 9.5 to 13), resulting in highly reductive properties, without being caustic and without changing the desirable properties of the aquatic species kept frozen.

In one aspect, the formula to calculate the final ORP during the mix is as follows: ORP (of the mixture)=IORP× (weight REICE/(weight of water+weight of REICE)). IORP is the initial ORP of the restructured water to be converted to ice. Actual ORP (of the mixture) may vary from the calculated ORP by +15%. The specific density of fresh water is considered equal to 1.0 (kg/liter) at 4.0 degrees Celsius, equivalent to 62.4 lbs/cubic feet at 39.2 degrees Fahrenheit. This formula is valid for any existing system or process used to produce ice. It is also useful for freezing fresh water, man-made saltwater, and sea water. The water to be frozen is in these processes is under atmospheric pressure (open tank, channel or pipe). Normally, the water is restructured in the same tank, container where it is to be frozen, or in a preliminary tank that feeds the system.

The steps in the process to produce REICE are substantially similar to the general restructuring process described hereinabove. If the source is fresh water to be frozen, then FLPH=Y×111.9×FGPM, Y=1+ (IORP/30). With minimum retention time of fresh water 15 minutes. Minimum ORP obtained after 15 minutes is (−290 mv). Additionally, C2=1.6×Y×VW, where C2 value is obtained in milliliters and VW value is in liters. If the source is natural or synthetic salt water to be frozen, then FLPH=Y×111.9×FGPM, Y=1+ (IORP/300). With minimum retention time of fresh water 30 minutes. Minimum ORP obtained after 30 minutes is (−300 mv). Additionally, C2=1.6×Y×VW.

Another aspect of the restructured water process is the preservation and prolongation of shelf-life of aquatic species. Shelf life is a constant challenge and a risk for all the aquatic species industries. The use of high oxidants with no residual effect (ozone and UV light) is very common now. The well-known problem is again, the non-residual effect risking contamination at any moment. The industry cannot use high concentrations of oxidants with residual effect, because the end product has a different flavor, taste, odor, etc. Using restructured water combined with REICE secures prevention and control of most of the contamination coming from fungi and bacteria. Washing and spraying restructured water covering areas of production, handling, storage and distribution definitely introduces a secure method. This restructured water can be used either by itself alone and/or combined with the conventional chemicals used in the processes of washing, prevention and control of bacteria and fungi. If combined, it enhances the inherent disinfecting and fungicidal properties of the conventional chemicals used.

In one embodiment, FLPH=Y×223.8×FGPM, where Y=1+ (IORP/470). Only fresh water quality or better must be used for this application. Minimum required contact time of C1 in the preparation tank: 20 minutes. Minimum ORP after 20 minutes is minimum (−290 mv). Further, C2=1.6× Y×VW.

Reducing Application as an Emergency System when Oxygen is Critically Low or Contamination Like Ammonia is at Toxic Levels This method is complementary to any other emergency methods existing in this niche of aquatic species. It works for both, salt water and fresh species. It can also be used only by itself. The reducing chemical and electrical properties of the infusion of the water gas neutralize most if not all the oxidation processes for a specific period of time. Tests conducted with different aquatic species (fresh and salt water) show that this method replaces for up to 72 hours the conventional methods of water treatment for the aquatic species (fresh, ocean and or man-made salt waters).

All living aquatic macro species (shrimp, fish, crustaceans, etc) harvested for human consumption constantly consume oxygen for their internal oxidation (synthesis) processes. None of them can live without a minimum concentration of oxygen in the liquid where they live (fresh, ocean or man-made salt waters). The amount of dissolved oxygen in water is counted in parts per million (ppm). Less than 3 to 4 ppm of dissolved oxygen is considered a very dangerous limit. An additional problem for the macro aquatic aerobic species is that algae, plants, microorganisms and contamination present in water also demand oxygen to oxidize themselves. Oxygen demand (chemical or biochemical) is then the problem.

Conventional water treatment systems remove the oxygen demand via chemical reactions or microorganisms. In indoor facilities, oxygen demand in the water tanks is often too high because of the presence of fecal matter, nitrogen compounds, and an excess of organic food that has not been consumed. These problems become critical upon the failure of the system that provides oxygen (or air) to the aquatic system. It is also critical when the water filtration/treatment systems fail.

The death of the species can then occur in a matter of minutes. This disclosure describes how the restructuring process becomes an alternate emergency system that stops the oxidation processes and neutralizes the ammonia problems. The method consists of constantly restructuring the water using the formula above. It is highly recommended to inject air or pure oxygen as soon as possible to increase the effectiveness of this emergency method. This is a simple recirculating method based combined with our water gas technology. In one embodiment, FLPH=Y×223.8×FGPM, where Y=1+ (IORP/470). Minimum required contact time of C1 in the preparation tank is greater than or equal to 20 minutes. Minimum ORP after 20 minutes is (−400 mv) or more negative.

Examples

Without further elaboration, it is believed that one skilled in the art can, based on the above description, utilize the present disclosure to its fullest extent. To facilitate a better understanding of the embodiments of the present disclosure, the following examples of representative embodiments are given. In no way should the following examples be read to limit, or to define, the scope of the disclosure. The following specific examples, i.e., Examples 1-9, are therefore to be construed as merely illustrative, and not limitative of the remainder of the disclosure in any way whatsoever. All publications cited herein are incorporated by reference in their entirety.

Example 1. Electrolytic Production of a Reducing Gas

An activator solution was prepared by combining 200 grams of activator in 500 ml of water in a reaction chamber of a ducted electrolytic wet cell working under 110 or 220 AC volts input and between 20-30 DC volts output. The activator was formed of 49±0.5 wt % potassium hydrate (Dupont, BASF, or PPG USA), 0.5±0.1 wt % magnesium sulfate (Dupont, BASF, or PPG USA), 49±0.5 wt % sodium oxidanide (Dupont, BASF, or PPG USA), and 0.5±0.1 wt % alkaline sodium silicate complex (described herein above). Prepare of the activator solution comprised providing 500 ml of water in the reaction chamber and first mixing the magnesium sulfate and alkaline sodium silicate complex in the water followed by stirring for 30 seconds. Next, the potassium hydrate and the sodium oxidanide were added into the mixture and stirred for an additional 30 seconds. Water was then added in the reaction chamber until a mark indicating a maximum fill level was reached. A direct current of 24.65±0.12 V was applied to the electrolytic cell and a reducing gas was produced. After production of the reducing gas initiated, the pressure of the reaction chamber was reduced to a pressure of 0.5±0.05 bar and the electrolytic reaction was continued producing reducing gas at a rate of about 2.2 liters/minute.

Example 2. Infusion of Reducing Gas into a Liquid

Reducing gas produced by the process of Example 1 was injected into 250 ml of reverse osmosis filtered water using a ½ inch standard rock diffuser (AquaCave or American Aquariums). The reduction potential (ORP) was measured periodically using a calibrated Hanna meter (HA 98121, Hannah Instruments, Ann Arbor, Michigan, USA), and infusion was terminated when the ORP was less than (−) 150 mV for at least 2 minutes. The initial ORP prior to infusion was (+) 120±5 mV. After the infusion process, the final ORP was −145±3 mV.

Example 3. Production of a Composite Reducing Liquid

Reducing gas produced by the process of Example 1 was infused into 250 ml of reverse osmosis water using a ½ inch standard rock diffuser at a rate of 1.5 liters/minutes at 4.0 psi output. Alkaline sodium silicate complex (SSC) having a putative empirical formula of $Na_{8.2}Si_{4.4}H_{97}O_{17.6}$ was added dropwise to provide a final concentration of 0.64 mg/l. The reduction potential (ORP) was measured periodically using a calibrated Hanna meter, and infusion was terminated when the ORP was less than (−) 150 mV for at least 2 minutes. The initial ORP prior to infusion was +120±5 mV. After the infusion process, the final ORP of the composite reducing liquid was −195±3 mV and the final pH of the composite reducing liquid was 10.45±0.05.

The results show that the combination of reducing gas and alkaline sodium silicate complex thus show an unexpected effect of providing a strong reduction potential. In addition, the composite reducing liquid has an "alkaline" property without having to add caustic species such as NaOH, KOH, and $NaHCO_3$.

The reducing gas was analyzed by gas chromatography and the results showed that the reducing gas had a composition that is 2 parts of monatomic Hydrogen and 1 part monatomic Oxygen. The infused reducing liquid of Example 2 was analyzed by infrared spectroscopy (values were obtained comparing intensity and wave numbers in cm-1). FIG. 1 shows an infrared spectrum of reverse osmosis water infused with the reducing gas (solid line) in comparison to that for reverse osmosis water (dashed line). It can be seen that infusion of the reducing gas changes the structure of the liquid in which it is infused.

Example 4. Production of a Ready to Drink Beverage

In the first step, 75 liters per hour of reducing water gas and 2.5 mg per liter of reducing metasilicate (SSC) under normal conditions of temperature and pressure were added to the tank that contains the RTD supermarket brand orange juice from concentrate, immediately before the bottling process. Next, the system used is following procedure similar to FIG. 2. Then, turbulent conditions were produced by cavitation, wherein the cavitation is conducted using a propeller at a rate of at least about 800±35 RPM. In order to obtain a value of −300 mV of ORP, an initial contact time of between 25 to 35 minutes was required. Then, a minimum retention time of 30 minutes at −300 mV is required.

The second step involved securing the properties of restructured water before the bottling process. Once retention time of 30 minutes was reached with a minimum of −300 mV and the desired pH value of 7.0 is reached, the restructured water is maintained out of the reach of solar rays, potential air contamination, or other forms of undesirable contamination. This was achieved by keeping the restructured RTD in the water tank perfectly sealed. It is preferable to bottle the restructured RTD within the next 4 hours after the restructuring process and RT are completed.

The third step involves the infusion, with a constant flow, of the reducing gas right before automatically sealing the cap of each bottle. The pressure of infusion of the gas is between 3.5 and 4.0 PSI at normal temperature and atmospheric pressure. An increase of pressure needs to be considered by adding 0.20 PSI per every 3000 (three thousand) feet of increase in altitude. No corrections are needed for variations in temperature and humidity, as long as the freezing point is not reached.

| RTD: orange juice (supermarket brand) from concentrate | |
|---|---|
| Initial ORP: +380 mv | Initial pH: 4.16. |
| Final ORP: −328 mv | Final pH: 7.56 |

Example 5. Pilot Study Evaluating the Effects of RLS+Hydrogas-Infused Water (AI-Water) in Healthy Individuals A study was conducted at the Salgado Institute of Integrative Health to study the effects of reformed liquid silica (RLS), also known as SSC, and Hydrogas-infused water (AL-WATER) in healthy individuals. The primary outcomes to be observed included urine pH and urine specific gravity in 16 healthy volunteers (14 women, 2 men, aged between 29 and 50). Individuals were asked to drink 1 liter of AL-WATER per day for 7 consecutive days. Urine pH and Urine specific gravity was evaluated with dip-stick method (Urinalysis Test Strips, USA). The first sample was taken before the individuals consumed AL-WATER and served as the baseline for the study. Subsequent samples were collected daily at the same time of the day (9 am) for seven days.

Figure 3A:
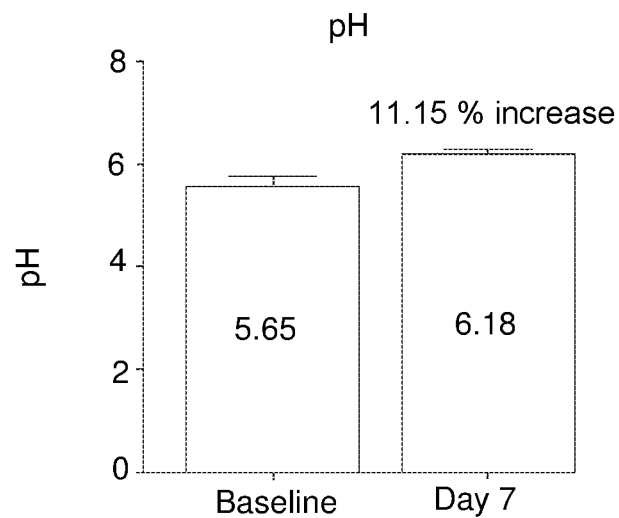
FIG. 3A describes pH data from a pilot study conducted studying the effects of AL-Water, described herein in Example 5.
Figure 3B:
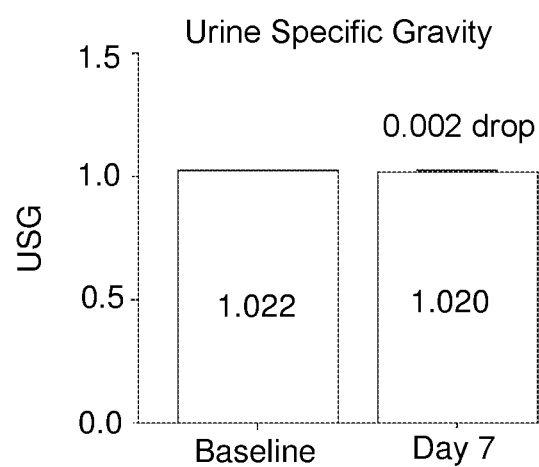
FIG. 3B describes specific gravity data of urine samples from a pilot study conducted studying the effects of AL-Water, described herein in Example 5.

After 7 days of drinking AL Water there was an 11.15% increase in urine pH. From 5.56 to 6.18 (FIG. 3A). The average pH of urine in the medical arts is well understood to be around 6.0. Participants mean pH at baseline was below average and increased after 7 days of consuming AL-WATER. Urine specific gravity had an insignificant drop, from 1.022 to 1.020 (FIG. 3B). Values between 1.002 and 1.030 are recognized as within normal range, suggesting that study participants had normal kidney function. The study concluded that consumption of 1 liter a day for 7 days of AL-Water induced an increase in 11.15% in urine pH (indicating less urine acidity) without interfering with kidney function. An increase in pH correlates to a lower concentration of hydrogen ions, which also translates into lower (more negative) ORP values.

Example 6. Uses Related to Laundry

A series of tests on the efficacy of different "formulations" were tested in an industrial laundry setting (with Tunnel Washers). The parameters evaluated were:

A—Whiteness Degree (Effective value: >80)
B—Yellowness (Effective value: <−2.0)
C—Blood Stain Removal (Effective value: >40)
D—Soil Removal (Effective value: >28)
E—Bleach Effectiveness (Effective value: >52)

In this study, different formulations of reducing gas and RLS were evaluated based on parameters described above. The only "formulation" that yielded effective scores in all evaluation parameters (except blood stain removal) was Hydrogas+2 ounces of liquid reformed silica (SSC)+2 ounces of regular detergent added to the first tunnel and 0.65 ounces of detergent added to tunnel 8 (Gas+2ozRLS+2oz-Det. Front+0.65Det@8). In industrial laundry uses, the applied combination of SSC and the reducing gas decreases the consumption of approved detergents by 80%. Additionally the mix has better bleaching properties compared to approved conventional bleaching chemicals currently used in this industry.

Example 7. Study in Barramundi Tanks

A study was conducted to gather initial data measuring the time to restructure and achieve high negative ORP in large water tanks containing Barramundi fish (Lates calcarifer). The primary objective of this study was to neutralize the effect of nitrates and ammonia in the water, which is a major problem with indoor farming of Barramundi and other aquatic species on a large scale. As fish tanks become more densely populated, fecal matter and unconsumed food within the tanks causes a spike in toxic ammonia which quickly increases mortality offish inside the tank. Adding antioxidant chemicals have both known and unknown undesirable effects in fish. The restructuring process provides a non-toxic and largely chemical free solution in decreasing nitrates inside fish tanks.

Figure 4:
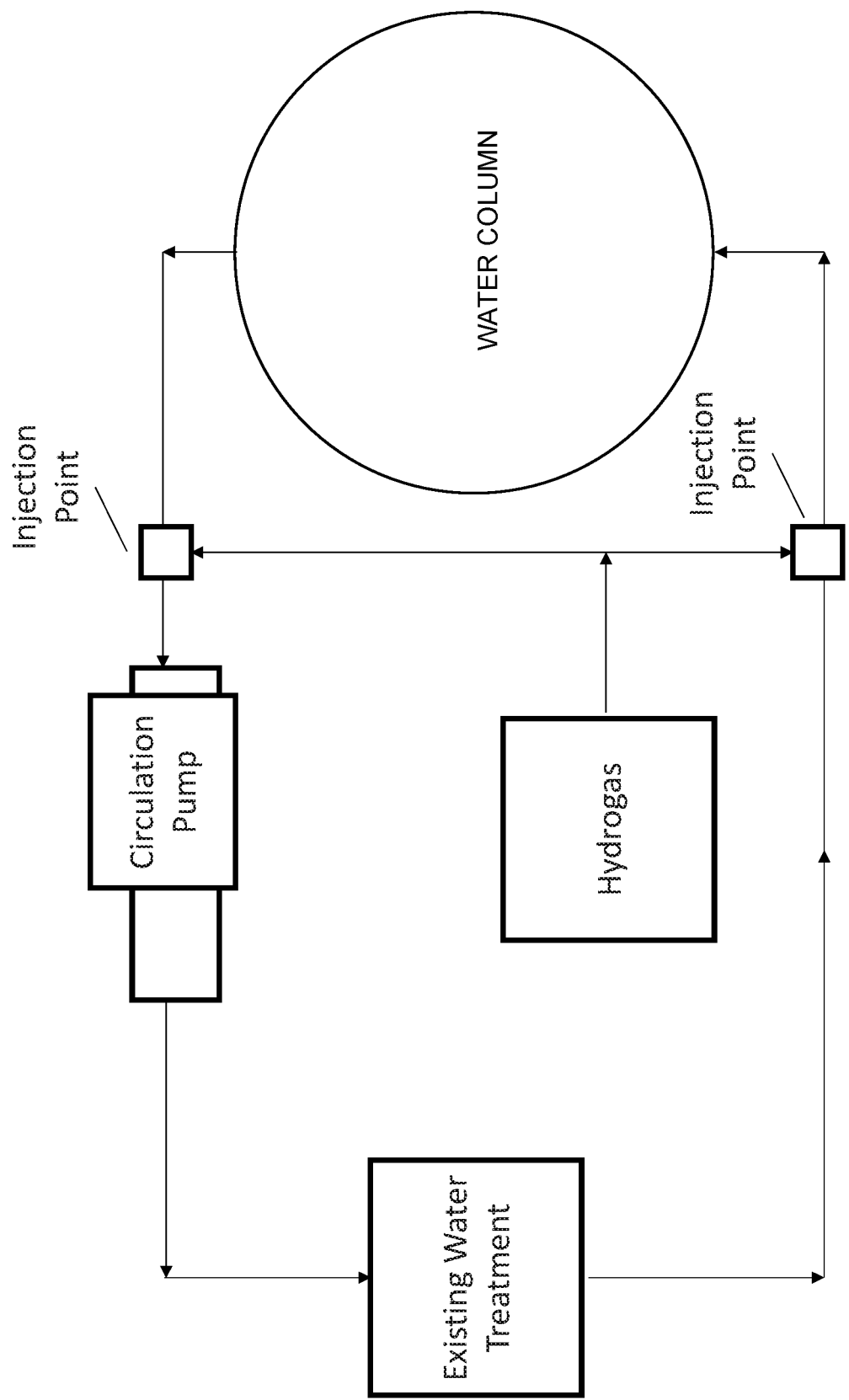
FIG. 4 is a schematic of an exemplary system for performing the methods described herein in Example 7. The system is used to perform a process in which a liquid metasilicate is injected into a water tank after it has been treated, and in which a reducing gas is injected into the same water container, for the cultivation of aquatic species.

FIG. 4 is a schematic showing an exemplary system is used to perform a process in which a liquid metasilicate is injected into a water tank after it has been treated, and by which a reducing gas is injected into the same water container, for the cultivation of aquatic species.

Researchers put approximately 150 Barramundi fish in a 5 gallon test tank (the "Test Tank") and then another 150 in a second tank (the "Control Tank"). Then HydroGas was injected into the Test Tank and analyzed for over 27 hours. Hydrogas is a strong reducing agent (anti-oxidant), or chemical neutralizer that was expected to cease chemical oxygen demand in the Test Tank. After infusion of the reducing HydroGas, the ORP was measured and the average charge was −430 mV. The negative ORP was maintained by intermittently bubbling HydroGas throughout the whole test. Oxygen demand was measured in two forms. The first is Biological Oxygen Demand (BOD), which measures the amount of dissolved oxygen consumed by the fish. The second form is Chemical Oxygen demand (COD), which measures the amount of oxygen consumed by chemical oxidants such as nitrates and ammonia. Fish mortality increased as oxygen levels in their environment decreases. Fecal matter and unconsumed food immediately begin the process of oxidation, or deterioration and used up oxygen.

By not changing or recirculating the water in our Test Tank for over 27 hours, researchers were able to simulate a week's worth of nitrate production; the water in the Test Tank was observed to be opaque to the naked eye. Nitrate levels of over 250 mg/liter is known to have increased mortality for in Barramundi. The nitrate testing equipment at the farm could detect levels up to 3000 mg/liter. At the end of the 27 hours, the tester could not register the amount of nitrates in the Test Tank because it was above the 3000 mg/l range.

The Control Tank was changed every 2 hours in order to maintain survival for these smaller fish, reducing the production of lethal nitrates and ammonia from food and fecal matter. The initial nitrate level was 175 mg/liter in each of the Control and Test Tanks at the beginning of the experiment. In the test tank the dissolved oxygen was only being consumed by the fish because everything else in the tank was expected to be stopped from the oxidative process. After implementing the restructuring process, the nitrate level in the Test Tank was above 3000 mg/liter under atmospheric conditions with an ORP value of −450 mV. Despite the high nitrate levels, the Barramundi were observed to not show any physical manifestations of distress and were in a relaxed state allowing the researchers to physically pet the fish. This is because the toxins' COD was neutralized. Additionally, the study established that it took 52 seconds to restructure a 500 gallon tank and turn it from a +240 mV ORP reading to a negative reading using a combination of a high flow pump and dual static mixers to infuse the gas much more efficiently. Further, an ORP of −400 mV was achieved in within 5 minutes. Based on the results, the described restructuring process is expected to yield similar results when implemented under a larger industrial scale, such as in a 65,000 gallon tank.

Example 8. Example Standard Operating Procedure for Restructuring RTD Beverages Using the Blue Box System Operating Conditions:
 Temperature: 7.3 to 48.9 degrees Celsius (45 to 120 degrees Fahrenheit)
 Humidity Levels: 10% to 70% (Non-Condensing)
Storage Conditions:
 Temperature: 7.3 to 48.9 degrees Celsius (45 to 120 degrees Fahrenheit)
Humidity Levels: 10% to 100% (Non-Condensing)

Figure 5:
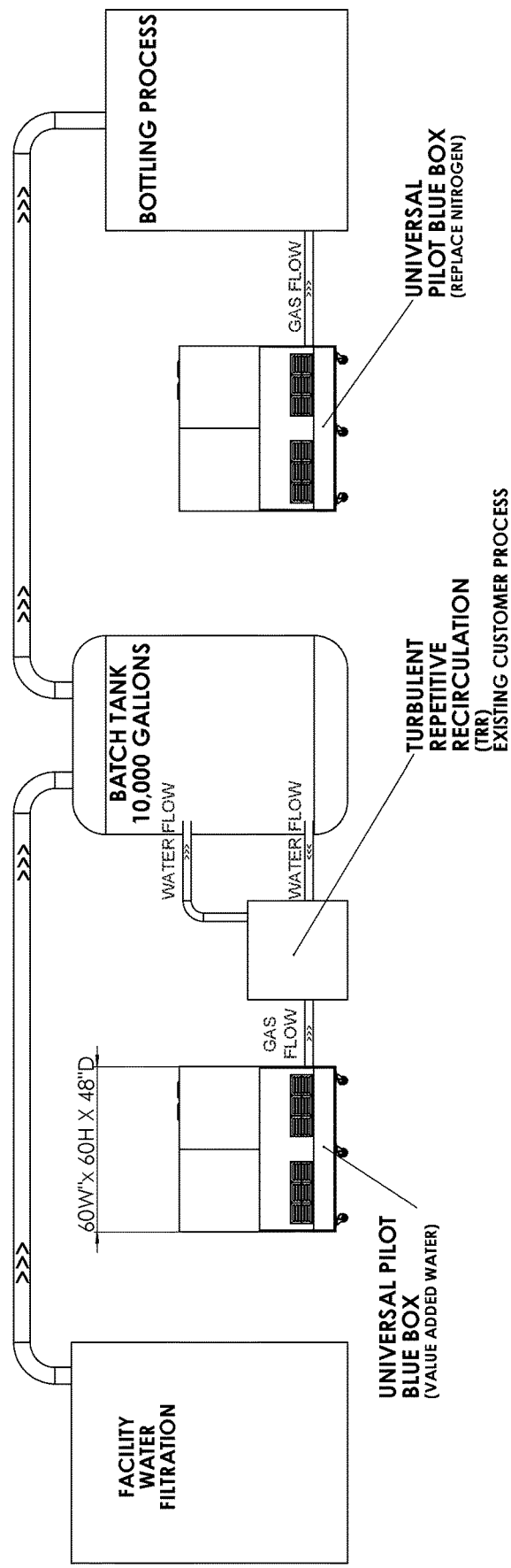
FIG. 5 is a schematic of an exemplary system for performing the methods, described herein in Example 8. The system is used to perform a process in which a liquid metasilicate is injected into a water tank after it has been treated, and in which a reducing gas is injected into the same water container, for the production of ready to drink beverages.

FIG. 5 is a schematic describing a "Blue Box" system used to perform the restructuring process. The blue box contains the reducing gas producing reactor and a dosification system to inject the liquid metasilicate in the batch tank. In order to restructure the sealed Batch Tank containing up to 10,000 gallons of water, the water in the tank is constantly recirculated using a conventional high flow, low pressure water pump. The blue box constantly delivers the reducing gas that goes to the suction of the pump. The blue box delivers constantly the liquid metasilicate via a dosifying pump in to the Batch Tank. The water in the batch tank, after a specific precalculated time passes, becomes a reduced/restructured liquid. Once the expected values of negative ORP and high pH are achieved, the reduced/restructured liquid then flows into the bottling process. Another Blue Box system is connected to the bottling process releasing additional reducing gas before the bottle cap is placed and sealed.

Procedure:
1. The equipment (BLUE BOX) arrives at the bottling facility at a minimum of 72 hours prior to the bottling date ("DATE 0").
2. AIM's engineering and technical team arrive at the bottling facility to start tests and calibrations at a minimum of 48 hours prior to "DATE 0."
3. Reverse Osmosis water (RO water) is used in the process. RO water must be in compliance with FDA Inspection Technical Guides, Number: 36, dated Oct. 21, 1980 (last updated Aug. 26, 2014), available on the FDA's website for reference.
4. A 100 ml sample of the RO water is collected for quality control and stability tests.
5. Initial ORP and pH verification is conducted.
6. AIM GAS goes to a recirculating pump (1.0 to 9.0 HP) that will inject the gas into the tank and will recirculate for a minimum of 45 minutes. This will be prior to start the bottling process.
7. AIM liquid (SDS JD501) is added (Quantity TBD).
8. AIM GAS is conducted via a ¼ inch plastic hose from the BLUE BOX to the recirculating pump. Another hose goes from the BLUE BOX to the bottling equipment. This second hose goes to the nitrogen infusion equipment. AIM GAS is injected at the end of the filling of each bottle.
9. Restructuring process begins: Gas is introduced to the recirculating pump for a period of 30 minutes.
10. Final ORP and pH verification is conducted.*
11. A water sample is collected for quality control (100 ml) and stability tests.
12. Bottling process starts, making sure that AIM GAS is being injected at the end of the filling of each bottle.
13. Random samples of sealed bottles are taken to test for ORP and pH.

The dosification of the reducing AIM LIQUID is manual.

*Final ORP value requirement: −300 mv or a more negative value.

*Final pH value requirement: 9.65 or a higher value.

The BLUE BOX requires the following electrical deliveries: 220 volts, two phases and neutral, 30 Amps breaker.

Example 9. Restructured Water and Liquid Silica Improve Equine Stride Parameters: In Vivo Evaluation of Restructured Water and Reformed Liquid Silica This study was carried out as a 4 week blind randomized controlled trial to determine if there was a difference in stride parameters and joint mobility in horses prior to and after drinking the RW+reformed liquid silica (RLS) compared to drinking RW and if there was a significant difference between the two treatments. The trial consisted of 12 healthy horses, each serving as their own control in a crossover design. The horses were randomly split into two groups, where one group received the RW and the other received RW+RLS. All of the horses were healthy and sound before, during, and after the trial was completed. The study was approved by Writtle university college animal welfare and ethics committee.

The trial took place over a 4-week period of which the horses were trotted up in front of camera at week 0, week 2 and week 4. The horses were provided their allocated water treatment in the morning and afternoon every day for four weeks. All horses received 50 L of restructured water divided on two buckets containing 25 L. The water was treated for with hydro gas from the reactor with an air pump to assure circulation. The group provided with RW+Silica received 40 mL of Silica in each of the 25 L buckets. The machine used to make the negatively charged alkaline water was referred to as "Hydro gas and electro magnetically charged reformed liquid silica." This equipment was plugged into a power source and the 2 tubes were placed into a water tank to restructure the water. For this trial, a water station referred to as "restructered water (RW) with reformed liquid silica (RLS)" was used to change the pH of the water. The reformed liquid silica solution that had a pH of 13.7.

In order to collect kinematics data, video recordings were taken using a high speed camera that has a recording speed of 240 frames per second. The camera was set up 6 meters from the track that the horses walked through. The cones were placed 3 meters apart meaning that the distance being recorded was 6 meters. Twelve biomechanical markers were placed on specific points on the forelimb and hindlimb: The proximal portion of the (1) scapular spine, (2) greater humeral tuberosity, (3) proximal to the lateral proximal radial tuberosity, (4) the ulnar carpal bone, (5) the distal condyle of the third metacarpal bone, (6) the caudal portion of the tuber coxae, (7) greater trochanter, (8) proximal and cranial to the lateral tibial condyle, (9) calcaneal tuberosity, (10) the distal condyle of the third metatarsal bone (Plate 1 and 2). This method of marker placement is the same as various comparable kinematic studies (Clayton and Schamhardt, 2001; Mendez-Angulo etal., 2014). One handler was used for all horses to limit difference in human stride length, handling and to assure the horses were accustomed to the handler. Measurements were obtained of the horses' protraction on front limb and hind limb, stride length and joint range of motion of the carpus and hock using Quintic Biomechanics software. Only one person was performing the gait analysis in order to limit human error.

The independent variables of the study are the RW, RW+silica. The dependant variables are the horses' joint ROM and gait parameters. Data that were collected were stored on Excel and then transferred to IBM SPSS version 25 statistics software where it was tested for normality using the Shapiro-Wilk coefficient, the data were found to be normally distributed and therefore ANOVA repeated measures was used. There was found significant difference for both treatments before and after, however, no significant difference was found between the two treatments. Data was normally distributed as assessed by Shapiro-Wilk's test ($p>0.05$).

Figure 6A:
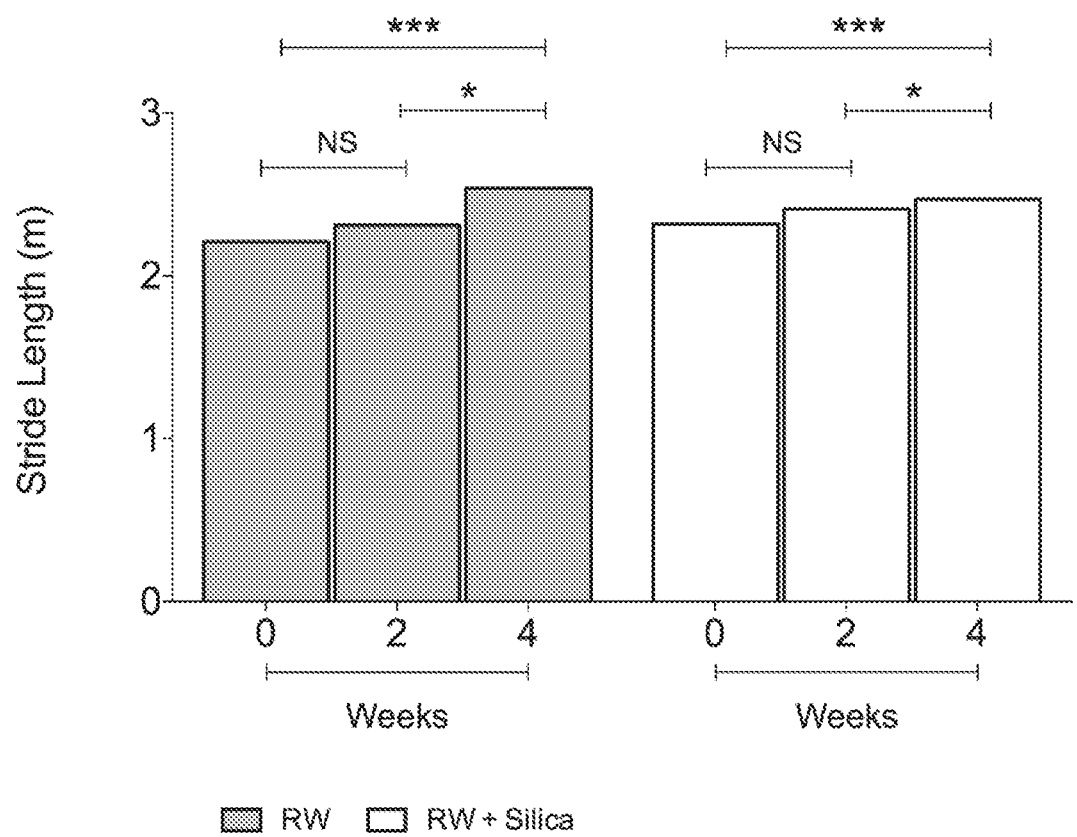
FIG. 6A describes the results of the equine study in Example 9 for the Stride Length parameter comparing the results RW and RW+Silica study arms.

Stride Strength (FIG. 6A). RW treatment increased stride length from 2.21±0.29 meters (Week 0), to 2.31±0.29 meters (Week 2), and to 2.54±0.26 meters (Week 4). There was no statistically significant increase from W0 to W2 ($p>0.05$); but there was a statistically significant increase from W2 to W4 ($p<0.05$), as well as from W0 to W4 ($p<0.001$). RW+Silica increased stride length from 2.32±0.25 meters (Week 0), to 2.41±0.23 meters (Week 2) and to 2.47±0.29 meters (Week 4). There was no statistically significant increase from W0 to W2 ($p>0.05$); but there was a statistically significant increase from W2 to W4 ($p<0.05$), as well as from W0 to W4 ($p<0.001$). There was no statistically significant difference between RW and RW+Silica groups.

Figure 6B:
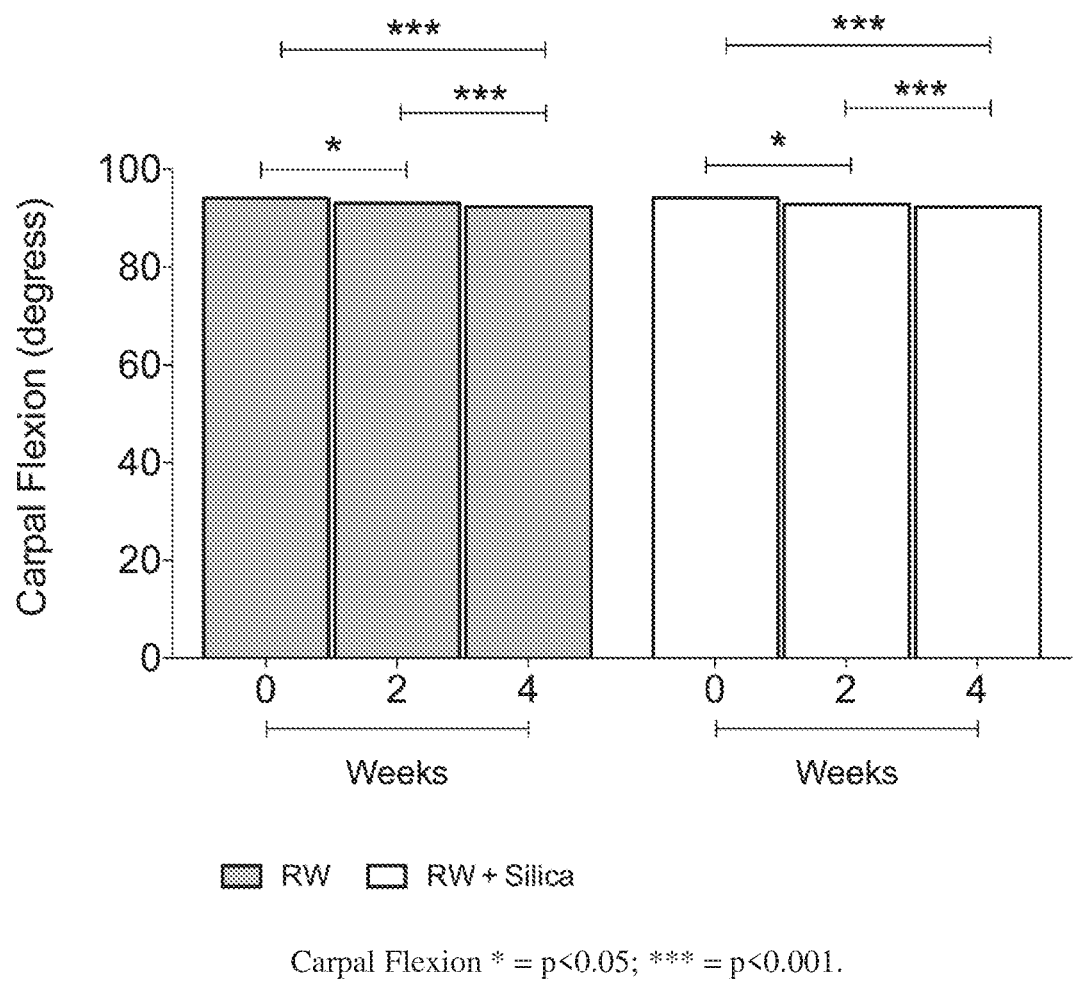
FIG. 6B describes the results of the equine study in Example 9 for the Carpal flexion parameter comparing the results RW and RW+Silica study arms.

Carpal flexion (FIG. 6B). RW treatment decreased carpal flexion from 94.10±1.87 degrees (Week 0), to 93.11±1.08 degrees (Week 2) and to 92.38±1.06 degrees (Week 4). There were statistically significant differences from W0 to W2 ($p<0.05$), from W2 to W4 ($p<0.001$), as well as from W0 to W4 ($p<0.001$). RW+Silica decreased carpal flexion from 94.18±1.23 degrees (Week 0), to 92.85±1.20 degrees (Week 2) and to 92.29±1.09 degrees (Week 4). There were statistically significant differences from W0 to W2 ($p<0.05$), from W2 to W4 ($p<0.001$), as well as from W0 to W4 ($p<0.001$). There was no statistically significant difference between RW and RW+Silica groups.

Figure 6C:
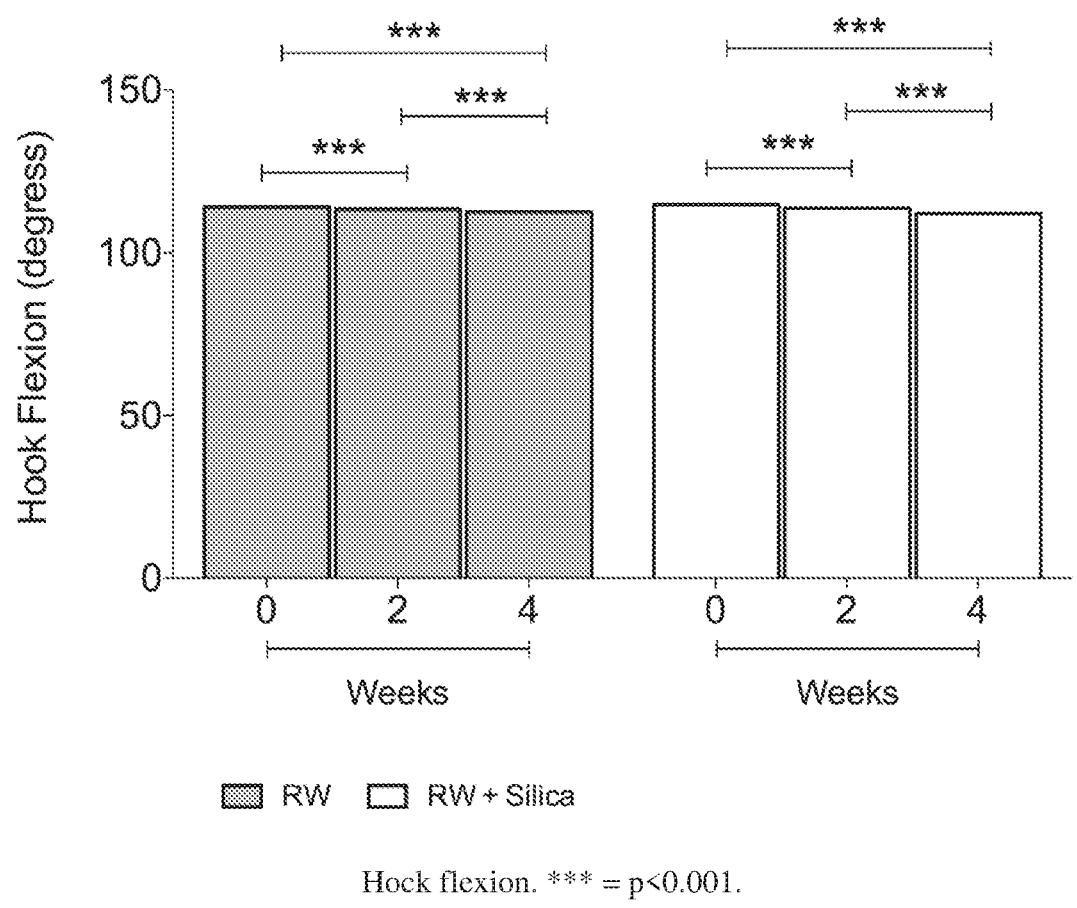
FIG. 6C describes the results of the equine study in Example 9 for the Hock flexion parameter comparing the results RW and RW+Silica study arms.

Hock flexion (FIG. 6C). RW treatment decreased Hock flexion from 114.18±2.39 degrees (Week 0), to 113.43±2.23 degrees (Week 2) and to 112.55±1.91 degrees (Week 4). There were statistically significant differences from W0 to W2 ($p<0.001$), from W2 to W4 ($p<0.001$), as well as from W0 to W4 ($p<0.001$). RW+Silica decreased Hock flexion from 114.83±1.54 degrees (Week 0), to 113.70±1.44 degrees (Week 2) and to 112.09±0.53 degrees (Week 4). There were statistically significant differences from W0 to W2 ($p<0.001$), from W2 to W4 ($p<0.001$), as well as from W0 to W4 ($p<0.001$). There was no statistically significant difference between RW and RW+Silica groups.

Figure 6D:
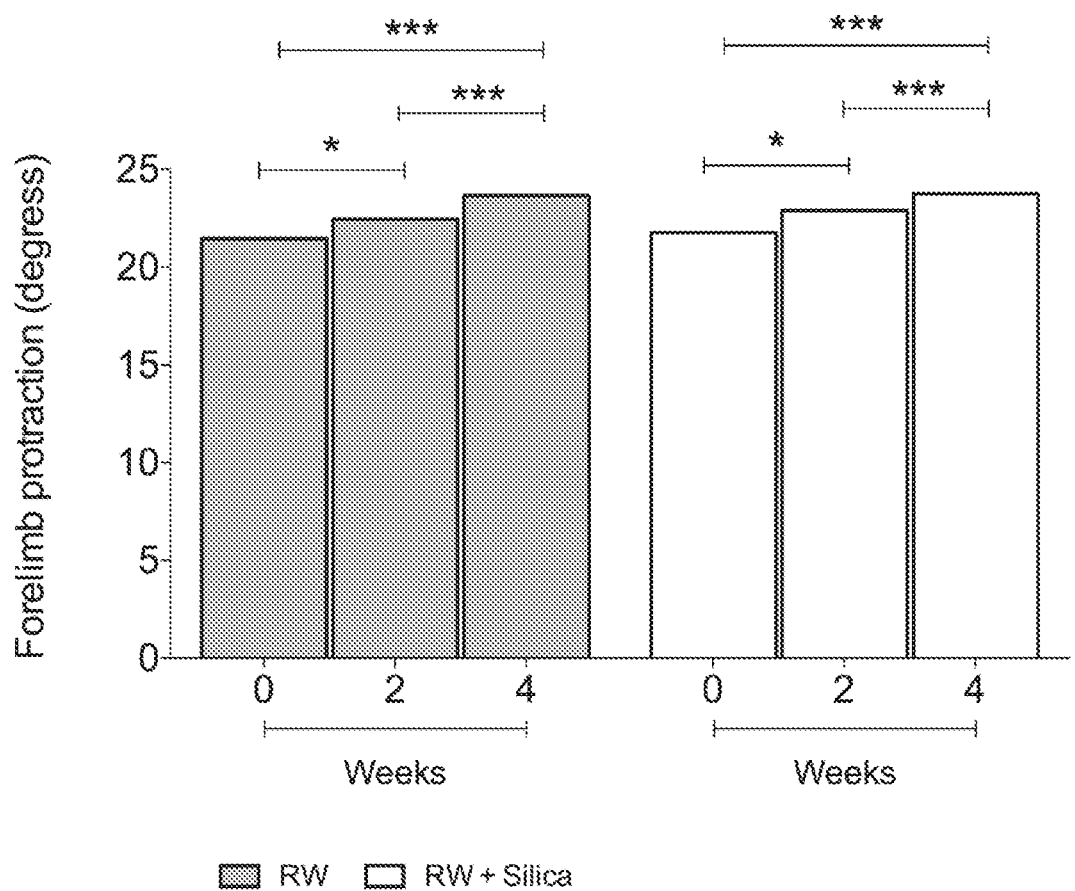
FIG. 6D describes the results of the equine study in Example 9 for the Forelimb protraction parameter comparing the results RW and RW+Silica study arms.

Forelimb protraction (FIG. 6D). RW treatment increased forelimb protraction from 21.45±2.18 degrees (Week 0), to 22.48±2.00 degrees (Week 2) and to 23.66±1.45 degrees (Week 4). There were statistically significant differences from W0 to W2 ($p<0.05$), from W2 to W4 ($p<0.001$), as well as from W0 to W4 ($p<0.001$). RW+Silica increased forelimb protraction from 21.75±1.32 degrees (Week 0), to 22.90±1.19 degrees (Week 2) and to 23.76±0.98 degrees (Week 4). There were statistically significant differences from W0 to W2 ($p<0.05$), from W2 to W4 ($p<0.001$), as well as from W0 to W4 ($p<0.001$). There was no statistically significant difference between RW and RW+Silica groups.

Figure 6E:
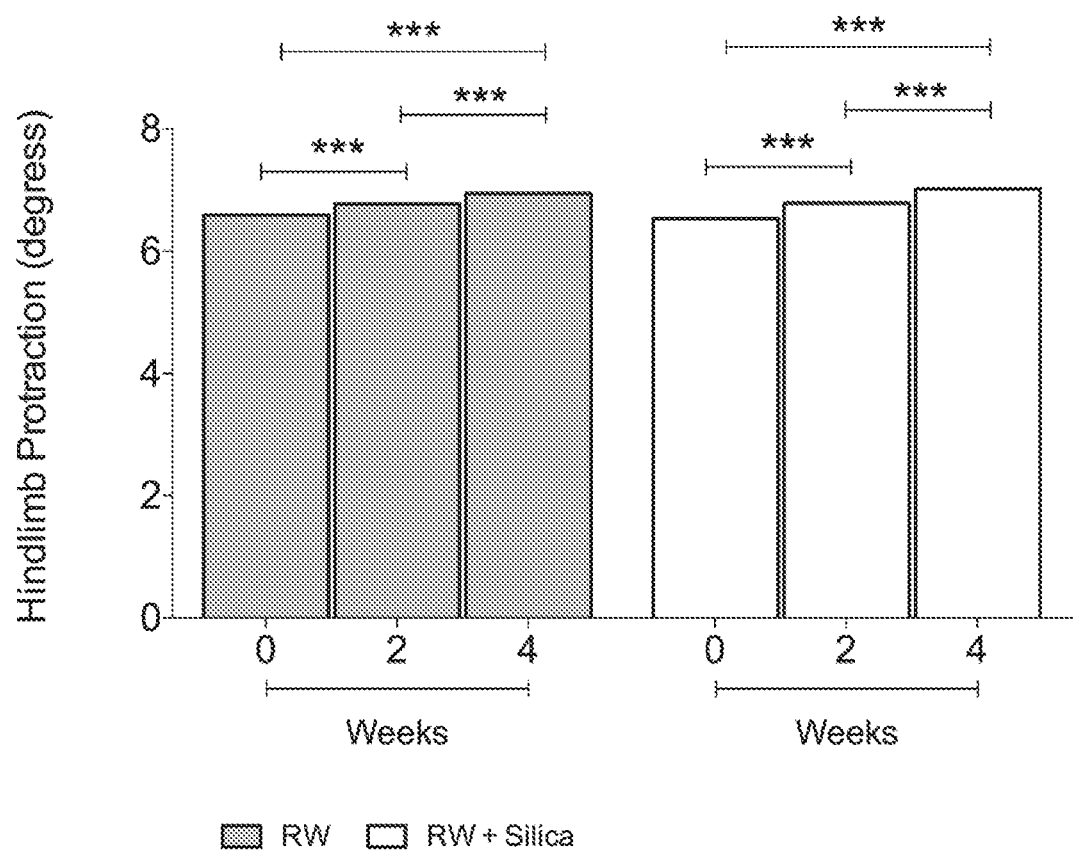
FIG. 6E describes the results of the equine study in Example 9 for the Hindlimb protraction parameter comparing the results RW and RW+Silica study arms.

Hindlimb protraction (FIG. 6E). RW treatment increased hindlimb protraction from 6.59±0.33 degrees (Week 0), to 6.78±0.35 degrees (Week 2) and to 6.95±0.28 degrees (Week 4). There were statistically significant differences from W0 to W2 ($p<0.001$), from W2 to W4 ($p<0.001$), as well as from W0 to W4 ($p<0.001$). RW+Silica increased hindlimb protraction from 6.53±0.36 degrees (Week 0), to 6.79±0.32 degrees (Week 2) and to 7.02±0.24 degrees (Week 4). There were statistically significant differences from W0 to W2 (p<0.001), from W2 to W4 (p<0.001), as well as from W0 to W4 (p<0.001). There was no statistically significant difference between RW and RW+Silica groups.

Further Considerations and Other Embodiments

While the disclosure has been described in connection with specific embodiments thereof, it will be understood that it is capable of further modifications and this application is intended to cover any variations, uses, or adaptations of the disclosure following, in general, the principles of the disclosure and including such departures from the disclosure that come within known or customary practice within the art to which the disclosure pertains and may be applied to the essential features hereinbefore set forth, and follows in the scope of the claims. Other embodiments are within the claims.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. A process for producing a reducing liquid, the process comprising:
   a) providing a liquid;
   b) providing a reducing gas and a first alkaline cationic silicate, wherein the reducing gas is produced by electrolysis with an activator present, wherein the activator comprises potassium hydrate, magnesium sulfate, sodium oxidanide, and a second alkaline cationic silicate; and
   c) infusing the reducing gas and the first alkaline cationic silicate into the liquid to produce the reducing liquid, wherein the reducing liquid has an oxidation reduction potential (ORP) value of about-100 mV or more negative.

2. The process of claim 1, wherein the liquid has a neutral or positive ORP value.

3. The process of claim 1, wherein the reducing gas is infused into the liquid under turbulent conditions.

4. The process of claim 1, wherein the contact time is at least about 3 seconds for the liquid and the reducing gas, or the liquid and the reducing gas and the first alkaline cationic silicate, or the liquid and the first alkaline cationic silicate.

5. The process of claim 4, wherein the contact time is at least about 30 mins.

6. The process of claim 1, wherein about 75 to about 120 liters per minute of the reducing gas is infused per every 60 gallons per minute of the liquid.

7. The process of claim 1, wherein the reducing liquid is substantially free of an oxidant.

8. The process of claim 1, wherein the reducing liquid is substantially free of calcium hypochlorite, sodium hypochlorite, gaseous chlorine, bromine, iodine, ozone, or ultraviolet light.

9. The process of claim 1, wherein the ORP value of the reducing liquid is about-200 mV to about-600 mV.

10. The process of claim 1, wherein the pH of the reducing liquid is greater than 7.0.

11. The process of claim 10, wherein the pH of the reducing liquid is 13.0 or higher.

12. The process of claim 1, wherein the liquid is potable water, non-potable water, fresh water, industrial water, salt water, or brackish water.

13. The process of claim 1, further comprising recycling the liquid through a treatment facility.

14. The process of claim 1, further comprising preventing exposure of the reducing liquid to solar rays or air contamination.

15. The process of claim 1, further comprising packaging the reducing liquid.

16. The process of claim 1, wherein the liquid is pre-filtered water, ultrafiltered water, or reverse osmosis water.

17. The process of claim 1, wherein at least one of the first alkaline cationic silicate and the second alkaline cationic silicate is selected from a group consisting of metal silicate, metasilicate, sodium silicate complex and reformed liquid silica.

18. The process of claim 17, wherein the sodium silicate complex is $Na_{8.2}Si_{4.4}H_{9.77}O_{17.6}$.

* * * * *